(12) United States Patent
Cripps et al.

(10) Patent No.: US 7,220,403 B2
(45) Date of Patent: *May 22, 2007

(54) PHARMACEUTICAL FORMULATION OF FLUTICASONE PROPIONATE

(75) Inventors: Alan Leslie Cripps, Ware (GB); Paul Johnson, Ware (GB)

(73) Assignee: Glaxo Group Limited, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/630,655

(22) Filed: Jul. 31, 2003

(65) Prior Publication Data

US 2004/0037783 A1    Feb. 26, 2004

Related U.S. Application Data

(63) Continuation of application No. 10/198,364, filed on Jul. 19, 2002, now Pat. No. 6,630,129, which is a continuation of application No. 09/659,492, filed on Sep. 11, 2000, now Pat. No. 6,479,035.

(30) Foreign Application Priority Data

| Sep. 11, 1999 | (GB) | ................................. | 9921396.9 |
| Jun. 13, 2000 | (GB) | ................................. | 0014451.9 |
| Jul. 28, 2000 | (GB) | ................................. | 0018654.4 |

(51) Int. Cl.
*A61K 9/00* (2006.01)
*A61K 9/12* (2006.01)

(52) U.S. Cl. .......................... 424/45; 424/43; 424/434; 128/200.14

(58) Field of Classification Search .................. 424/45, 424/46, 43, 434, 489; 514/826; 128/200.14
See application file for complete search history.

(56) References Cited

U.S. PATENT DOCUMENTS

| 4,243,548 | A   |   | 1/1981  | Heeb et al. ................. 252/305 |
| 5,653,962 | A   |   | 8/1997  | Akehurst, et al. |
| 5,736,124 | A   |   | 4/1998  | Akehurst et al. ............. 424/45 |
| 5,914,122 | A   | * | 6/1999  | Otterbeck et al. .......... 424/434 |
| 5,919,827 | A   |   | 7/1999  | Barberich, et al. |
| 6,004,537 | A   |   | 12/1999 | Cavanaugh, et al. |
| 6,241,969 | B1  |   | 6/2001  | Saidi et al. .................... 424/45 |
| 6,309,623 | B1  | * | 10/2001 | Weers et al. ................... 424/45 |
| 6,479,035 | B1  | * | 11/2002 | Cripps et al. ................. 424/45 |
| 6,630,129 | B2  | * | 10/2003 | Cripps et al. ................. 424/45 |

FOREIGN PATENT DOCUMENTS

| AU | B-90873/91 | 5/1992 |
| CA | 2094266 | 4/1998 |
| EP | 0 416 951 A | 3/1991 |
| EP | 94 13262 | 6/1994 |
| EP | 0 553 298 B1 | 11/1994 |
| EP | 00 30607 | 6/2000 |
| EP | 1084726 A2 | 3/2001 |
| GB | 2 235 627 A | 3/1991 |
| WO | WO 92/06675 | 4/1992 |
| WO | WO 93/11743 | 6/1993 |
| WO | WO 93/11745 A1 | 6/1993 |
| WO | WO 94/13262 | 6/1994 |
| WO | WO 96/32151 | 10/1996 |
| WO | WO 98/24420 | 6/1998 |
| WO | WO 98/56349 | 12/1998 |
| WO | WO 99/55600 A1 | 11/1999 |
| WO | WO 99/65464 | 12/1999 |
| WO | WO 00/06121 | 2/2000 |
| WO | WO 00/30607 | 6/2000 |
| WO | WO 00/48587 A1 | 8/2000 |
| WO | 01/37805 A1 | 5/2001 |
| WO | WO 01/37805 A1 | 5/2001 |
| WO | WO 01/58508 A2 | 8/2001 |

OTHER PUBLICATIONS

Davis et al, Physico-chemical studies on aerosol solutions for drug delivery II, water-propylene glycol-ethanol system, International Journal of Pharmaceutics, 1(1978) 85-93.*
Richard N. Dalby, et al., "Comparison of Output Particle Size Distributions from Pressurized Aerosols Formulated as Solutions or Suspensions", Pharmaceutical Research, 1988, vol. 5, No. 1, pp. 36-39.
S.S. Davis, "Physico-Chemical Studies on Aerosol Solutions for Drug Delivery I. Water-Propylene Glycol Systems", International Journal of Pharmaceutics, 1978, vol. 1, pp. 71-83.
S.S. Davis, "Physico-Chemical Studies on Aerosol Solutions for Drug Delivery II. Water-Propylene Glycol-Ethanol Systems", International Journal of Pharmaceutics, 1978, vol. 1, pp. 85-93.
Peter Zanan, et al., "The optimal particle size for β-adrenergic aerosols in mild asthmatics", International Journal of Pharmaceutics, 1994, vol. 107, pp. 211-217.
Peter Zanan, et al., "The optimal particle size for parasympathicolytic aerosols in mild asthmatics", International Journal of Pharmaceutics, 1995, vol. 114, pp. 111-115.
Peter Zanan, et al., "Optimal particle size for $β_2$ agonist and anticholinergic aerosols in patients with severe airflow obstruction", Thorax, 1996, vol. 51, pp. 977-980.

* cited by examiner

*Primary Examiner*—Sreeni Padmanabhan
*Assistant Examiner*—Mina Haghighatian
(74) *Attorney, Agent, or Firm*—Bacon & Thomas PLLC

(57) ABSTRACT

There is provided according to the invention a pharmaceutical aerosol formulation which comprises:
(i) fluticasone propionate and
(ii) a hydrofluoroalkane (HFA) propellant,
characterised in that the fluticasone propionate is completely dissolved in the formulation. The invention also provided canisters containing the formulation and uses thereof.

35 Claims, 19 Drawing Sheets

Figure 15

Cascade Impaction analysis of FP50µg/HFA134a solution aerosols containing various solubilising agents and 1% glycerol

Figure 18

Cascade Impaction analysis of FP25μg solution aerosols in HFA227 or HFA134a containing ethanol
(63μl valve; data normalised for 100μl valve)

PHARMACEUTICAL FORMULATION OF FLUTICASONE PROPIONATE

CROSS REFERENCE TO PRIOR APPLICATIONS

This application is a continuation application of U.S. application Ser. No. 10/198,364, filed Jul. 19, 2002 now U.S. Pat. No. 6,630,129 (of which the entire disclosure of the pending, prior application is hereby incorporated by reference), which application has been allowed and the Issue Fee paid on Jul. 24, 2003, which is a continuation of U.S. application Ser. No. 09/659,492, filed Sep. 11, 2000, which is now U.S. Pat. No. 6,479,035, granted on Nov. 12, 2002.

This is a U.S. patent application being filed under 37 C.F.R. 1.53(b) claiming priority to GB9921396.9 filed 11 Sep. 1999 in the United Kingdom; for which GB0014451.9 was filed 13 Jun. 2000 and GB0018654.4 was filed 28 Jul. 2000 in the United Kingdom.

BACKGROUND OF THE INVENTION

1. Field of the Invention

The present invention relates to a pharmaceutical formulation for use in the administration of medicaments by inhalation. In particular, this invention relates to a pharmaceutical formulation of fluticasone propionate for use in metered dose inhalers (MDI's). The invention also relates to methods for their preparation and to their use in therapy.

2. Description of the Background Art

Inhalers are well known devices for administering pharmaceutically active materials to the respiratory tract by inhalation. Such active materials commonly delivered by inhalation include bronchodilators such as β2 agonists and anticholinergics, corticosteroids, anti-allergics and other materials that may be efficiently administered by inhalation, thus increasing the therapeutic index and reducing side effects of the active material.

(6a, 11b, 16a, 17a)-6,9-difluoro-11-hydroxy-16-methyl-3-oxo-17-(1-oxopropoxy) androsta-1,4-diene-17-carbothioic acid, S-fluoromethyl ester was described as an antiinflammatory steroid by U.S. Pat. No. 4,335,121. This compound is also known by the generic name of fluticasone propionate and has since become widely known as a highly effective steroid in the treatment of inflammatory diseases, such as asthma and chronic obstructive pulmonary disease (COPD).

Metered dose inhalers (MDI's) are the most common type of a wide range of inhaler types and utilise a liquefied propellant to expel droplets containing the pharmaceutical product to the respiratory tract as an aerosol. MDI formulations ar generally characterised as solution formulations or suspenston formulations.

The most commonly used aerosol propellants for medicaments have been Freon 11 ($CCl_3F$) in admixture with Freon 12 ($CCl_2F_2$) and Freon 114 ($CF_2Cl.CF_2Cl$). However, these propellants are now believed to provoke the degradation of stratospheric ozone and their use is now being phased out to eliminate the use of all CFC containing aerosol propellants. There is thus a need to provide an aerosol formulation for medicaments which employ so called 'ozone-friendly' propellants.

Hydrofluoroalkanes (HFAs; known also as hydrofluorocarbons or HFCs) contain no chlorine and are considered less destructive to ozone and these are proposed substitutes for CFCs. In particular, 1,1,1,2-tetrafluoroethane (HFA 134a) and 1,1,1,2,3,3,3-heptafluoropropane (HFA 227) have been acknowledged to be the best candidates for non-CFC propellants.

The efficiency of an aerosol device, such as an MDI, is a function of the dose deposited at the appropriate site in the lungs. Deposition is affected by several factors, of which one of the most important is the aerodynamic particle size. Solid particles and/or droplets in an aerosol formulation can be characterised by their mass median aerodynamic diameter (MMAD, the diameter around which the mass aerodynamic diameters are distributed equally).

Particle deposition in the lung depends largely upon three physical mechanisms:
1. impaction, a function of particle inertia;
2. sedimentation due to gravity; and
3. diffusion resulting from Brownian motion of fine, submicrometer (<1 µm) particles.

The mass of the particles determines which of the three main mechanisms predominates.

The effective aerodynamic diameter is a function of the size, shape and density of the particles and will affect the magnitude of forces acting on them. For example, while inertial and gravitational effects increase with increasing particle size and particle density, the displacements produced by diffusion decrease. In practice, diffusion plays little part in deposition from pharmaceutical aerosols. Impaction and sedimentation can be assessed from a measurement of the MMAD which determines the displacement across streamlines under the influence of inertia and gravity, respectively.

Aerosol particles of equivalent MMAD and GSD (geometric standard deviation) have similar deposition in the lung irrespective of their composition. The GSD is a measure of the variability of the aerodynamic particle diameters.

For inhalation therapy there is a preference for aerosols in which the particles for inhalation have a diameter of about 0.5 to 5 µm. Particles which are larger than 5 µm in diameter are primarily deposited by inertial impaction in the orthopharynx, particles 0.5 to 5 µm in diameter, influenced mainly by gravity, are ideal for deposition in the conducting airways, and particles 0.5 to 3 µm in diameter are desirable for aerosol delivery to the lung periphery. Particles smaller-than 0.5 µm may be exhaled.

Respirable particles are generally considered to be those with aerodynamic diameters less than 5 µm. These particles, particularly those with a diameter of about 3 µm, are efficiently deposited in the lower respiratory tract by sedimentation.

It has been recently demonstrated in patients with mild and severe airflow obstruction that the particle size of choice for a β2 agonist or anticholinergic aerosol should be approximately 3 µm (Zaanen, P. et al, Int. J. Pharm. (1994) 107, 211–217, Int. J. Pharm. (1995)114, 111–115, Thorax (1996), 51, 977–980.)

Many of the factors relevant to the MMAD of particles are relevant to droplets and the additional factors of rate of solvent evaporation, and surface tension are also important.

In suspension formulations, particle size in principle is controlled during manufacture by the size to which the solid medicament is reduced, usually by micronisation. However, if the suspended drug has the slightest solubility in propellant, a process known as Ostwald Ripening can lead to particle size growth. Also, particles may have tendency to aggregate, or adhere to parts of the MDI eg. canister or valve. The effect of Ostwald ripening and particularly of drug deposition may be particularly severe for potent drugs (including fluticasone propionate) which need to be formulated in low doses. Solution formulations do not suffer from these disadvantages, but suffer from different ones in that particle or droplet size is both a function of rate of evaporation of the propellant from the formulation, and of the time between release of formulation from canister and the moment of inhalation. Thus, it may be subject to considerable variability and is generally hard to control.

Besides its impact on the therapeutic profile of a drug, the size of aerosol particles has an important impact on the side effect profile of a drug. For example, it is well known that the orthopharynx deposition of aerosol formulations of steroids can result in side effects such as candidiasis of mouth and throat. Accordingly, throat deposition of such aerosol formulations is generally to be avoided. Furthermore, a higher systemic exposure to the aerosol particles due to deep lung penetration can enhance the undesired systemic effects of certain drugs. For example, the systemic exposure to certain steroids can produce side effects on bone metabolism and growth.

SUMMARY OF THE INVENTION

Thus, according to the present invention we provide a pharmaceutical aerosol formulation for use in a metered dose inhaler, comprising (i) fluticasone propionate and (ii) a hydrofluoroalkane (HFA) propellant; and characterised in that the fluticasone propionate is completely dissolved in the formulation.

DETAILED DESCRIPTION OF THE INVENTION

The formulation according to the invention will generally contain a solubilisation agent to aid solubilisation of the fluticasone propionate in the formulation. Suitable solubilisation agents include propylene glycol and ethanol, preferably ethanol. Other suitable solubilisation agents include ethers (eg dimethyl ether). Alkanes may also be of use. A further solubilisation agent of interest is dimethoxymethane (methylal) which has good solvency properties. We have also found ethylacetate to be a solubilising agent with good solvency properties.

As a particular aspect of the present invention we provide a pharmaceutical aerosol formulation comprising (i) fluticasone propionate, (ii) a hydrofluoroalkane (HFA) propellant, (iii) a low volatility component to increase the mass median aerodynamic diameter (MMAD) of the aerosol particles on actuation of the inhaler and (iv) a solubilisation agent in sufficient quantity to solubilise the fluticasone propionate in the formulation.

The presence of the low volatility component in the solution formulation increases the fine particle mass (FPM) as defined by the content of stages 3–5 of an Andersen Cascade Impactor on actuation of the formulation relative to solutions formulations which omit this component. Solution formulations which omit the higher volatility component generally give rise to a particle size distribution which have a higher content of finer particles; such distributions generally do not match the distribution of the existing commercialised suspension formulations which contain CFC's and may therefore not be bio-equivalent.

Examples of HFA propellants include 1,1,1,2-tetrafluoroethane (HFA134a) and 1,1,1,2,3,3,3-heptafluoro-n-propane (HFA227) and mixtures thereof. The preferred propellant is 1,1,1,2-tetrafluoroethane (HFA134a). An alternative propellant of interest is 1,1,1,2,3,3,3-heptafluoro-n-propane (HFA227).

The preferred low volatility component is glycerol, propylene glycol or polyethyleneglycol (eg PEG 200 or PEG 400), especially glycerol. Polyethylene glycol is also of particular interest, especially PEG400. Preferably it is present in an amount of 0.5 to 3% (w/w), especially around 1% (w/w).

The preferred solubilisation agent is ethanol.

More specifically, the present invention can be defined as a pharmaceutical aerosol formulation which comprises:
(i) fluticasone propionate;
(ii) 1,1,1,2-tetrafluoroethane (HFA 134a);
(iii) 0.5-3% (w/w) glycerol; and
(iv) a solubilisation agent (particularly ethanol) in sufficient quantity to solubilise the fluticasone propionate in the formulation.

We prefer the formulation to be suitable for delivering a therapeutic amount of fluticasone propionate in one or two actuations. Preferably, the formulation will be suitable for delivering 25–250 μg per actuation, especially 25 μg, 50 μg, 125 μg or 250 μg per actuation. However, as mentioned in the foregoing, the amount of ethanol required to dissolve high concentrations of fluticasone propionate may tend to depress the vapour pressure of the propellant to an undesirable degree. The vapour pressure should desirably remain above around 50 psi. Therefore the formulation is most suitable for delivering 25–125 μg per actuation, especially 25–50 μg per actuation.

The formulation according to the invention will be used in association with a suitable metering valve. We prefer that the formulation is actuated by a metering valve capable of delivering a volume of between 50 μl and 100 μl, eg 50 μl or 63 μl. 1000 μl is also suitable. When a 50 μl metering volume is used, the final concentration of fluticasone propionate delivered per actuation would be 0.1% w/v (which equates to 0.1 g of fluticasone propionate per 100 ml of formulation) or approx. 0.083% w/w (which equates to 0.083 g of fluticasone propionate per 100 μg of formulation) for a 50 μg dose, 0.25% (w/v) or approx. 0.21% (w/w) for a 125 μg dose, 0.5% (w/v) or approx. 0.42% (w/w) for a 250 μg dose and 0.05% (w/v) or approx 0.042% (w/w) for a 25 μg dose. Wherein a 63 μl metering volume is used, the final concentration of fluticasone propionate delivered per actuation would be 0.079% (w/v) or approx. 0.067% (w/w) for a 50 μg dose, 0.198% (w/v) or approx. 0.167% (w/w) for a 125 μg dose, 0.397% (w/v) or approx. 0.333% (w/w) for a 250 μg dose and 0.04% (w/v) or approx. 0.033% (w/w) for a 25 μg dose. When a 100 μl metering volume is used, the final concentration of fluticasone propionate delivered per actuation would be 0.05% w/v (which equates to 0.05 g of fluticasone propionate per 100 ml of formulation) or approx. 0.042% w/w (which equates to 0.042 g of fluticasone propionate per 100 g of formulation) for a 50 μg dose, 0.125% (w/v) or approx. 0.11% (w/w) for a 125 μg dose, 0.25% (w/v) or approx. 0.21% (w/w) for a 250 μg dose and 0.025% (w/v) or approx. 0.021% (w/w) for a 25 μg dose. The previously quoted w/w figures are approximate in that they do not compensate in the mismatch in density between HFA134a and ethanol, however the precise figures may be readily determined.

The formulation is most suitable for concentrations of fluticasone propionate in the range 0.025 to 0.25% (w/v), preferably 0.025 to 0.15% (w/v), more preferably 0.035 to 0.15% (w/v), particularly 0.04 to 0.1% (w/v). A concentration of 0.025 to 0.04% (w/v) is also of particular interest. Formulations of the present invention containing such low concentrations of fluticasone propionate may have particular physical stability advantages relative to suspension formulations containing the same wherein particles of fluticasone propionate may be susceptible to Ostwald ripening or to drug deposition on the canister wall or on parts of the valve as discussed above. Drug deposition is especially problematic in low strength fluticasone propionate suspension formulations because the amount of drug lost through deposition on internal surfaces of the metered dose inhaler can represent a significant proportion of the total available drug and therefore have a significant effect on dosing uniformity through the life of the product. The solution formulations of the present invention overcome or substantially mitigate such disadvantages.

Use of a larger metering chamber eg 100 μl will generally be preferred.

We prefer the formulation to contain between 0.5 and 2% w/w, more preferably between 0.8 and 1.6% w/w, particularly between 1.0 and 1.6% w/w glycerol. Another range of particular interest is 0.5–1% (w/w) glycerol. We especially prefer to use 1.3% (w/w) glycerol. We also especially prefer to use 1.0% w/w glycerol.

Depending on the final concentration of fluticasone propionate in the formulation, the propellant, and the precise amount of low volatility component, the concentration of solubilisation agent (eg ethanol) required will vary. So as not to suppress the vapour pressure of the propellant to an undesirable extent, the amount of ethanol should preferably not exceed around 35%. The amount of ethanol will more preferably be in the range 5 to 30%, particularly 5 to 20%, more particularly 10 to 20%. A range of 7 to 16% w/w is also particularly preferred, more particularly 7 to 11% w/w.

When the concentration of fluticasone propionate is around 0.1% w/v and the propellant is 1,1,1,2-tetrafluoroethane, an amount of ethanol of 16–24% w/w eg 16–18% w/w, especially around 16% w/w is particularly suitable but is more preferably 20–22% w/w especially around 21% w/w. When the concentration of fluticasone propionate is around 0.05% w/v and the propellant is 1,1,1,2-tetrafluoroethane, an amount of ethanol of 7–11% w/w eg 7–8% w/w, especially around 7% w/w is particularly suitable but is more preferably 9–11% w/w especially around 10% w/w. When the concentration of fluticasone propionate is around 0.079% w/v and the propellant is 1,1,1,2-tetrafluoroethane, an amount of ethanol of 15–17% w/w especially around 16% is suitable. When the concentration of fluticasone propionate is around 0.198% w/v and the propellant is 1,1,1,2-tetrafluoroethane, an amount of ethanol of 34–36% w/w eg around 35% is suitable. When the concentration of fluticasone propionate is around 0.025% w/v and the propellant is 1,1,1,2-tetrafluoroethane, an amount of ethanol of 7–9% w/w especially around 8%, more preferably around 7% is suitable.

When the concentration of fluticasone propionate is around 0.0250%, w/v and the propellant is 1,1,1,2,3,3,3-heptafluoro-n-propane, an amount of ethanol of 13–15% w/w especially around 14% is suitable. When the concentration of fluticasone propionate is around 0.05% w/v and the propellant is 1,1,1,2,3,3,3-heptafluoro-n-propane, an amount of ethanol of 17–19% w/w especially around 18% is suitable.

When the concentration of fluticasone propionate is around 0.05% w/v and the propellant is 1,1,1,2-tetrafluoroethane, an amount of ethylacetate as solubilisation agent of 13–16% w/w especially around 15% is suitable. When the concentration of fluticasone propionate is around 0.05% w/v and the propellant is 1,1,1,2-tetrafluoroethane, an amount of dimethoxymethane (methylal) as solubilisation agent of 13–16% w/w especially around 15% is suitable.

The above generally described formulations are particularly preferred in conjunction with 1.0–1.6% w/w glycerol, particularly 1.0% w/w glycerol or 1.3% w/w glycerol.

Formulations according to the invention which are free of surfactants are preferred. Formulations according to the invention which are free of all excipients besides the solubilisation agent (eg ethanol), low volatility component (such as glycerol) and the propellant are particularly preferred.

Formulations according to the invention will preferably contain fluticasone propionate as the only medicament. However formulations which contain medicaments in addition to fluticasone propionate such as beta adrenergic agonists and anti-cholinergic compounds may also be contemplated.

The pharmaceutical composition according to the present invention may be filled into canisters suitable for delivering pharmaceutical aerosol formulations. Canisters generally comprise a container capable of withstanding the vapour pressure of the HFA propellant, such as plastic or plastic-coated glass bottle or preferably a metal can, for example an aluminium can which may optionally be anodised, lacquer-coated and/or plastic-coated, which container is closed with a metering valve. It may be preferred that canisters be coated with a fluorocarbon polymer as described in WO 96/32151, for example, a co-polymer of polyethersulphone (PES) and polytetrafluoroethylene (PTFE). Another polymer for coating that may be contemplated is FEP (fluorinated ethylene propylene). The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Thermoplastic elastomer valves as described in WO92/11190 and valves containing EPDM rubber as described in WO95/02651 are especially suitable. Suitable valves are commercially available from manufacturers well known in the aerosol industry, for example, from Valois, France (eg. DF10, DF30, DF60), Bespak plc, UK (eg. BK300, BK356, BK357) and 3M-Neotechnic Ltd, UK (eg. Spraymiser™). The DF31 valve of Valois, France is also suitable.

Valve seals, especially the gasket seal, and also the seals around the metering chamber, will preferably be manufactured of a material which is inert to and resists extraction into the contents of the formulation, especially when the contents include ethanol.

Valve materials, especially the material of manufacture of the metering chamber, will preferably be manufactured of a material which is inert to and resists distortion by contents of the formulation, especially when the contents include ethanol. Particularly suitable materials for use in manufacture of the metering chamber include polyesters eg polybutyleneterephthalate (PBT) and acetals, especially PBT.

Materials of manufacture of the metering chamber and/or the valve stem may desirably be fluorinated, partially fluorinated or impregnated with fluorine containing substances in order to resist drug deposition.

Valves which are entirely or substantially composed of metal components (eg Spraymiser, 3M-Neotechnic) are especially preferred for use according to the invention.

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The medicament is added to a charge vessel and a mixture of ethanol, low volatility component and liquefied propellant is pressure filled through the charge vessel into a manufacturing vessel. An aliquot of the formulation is then filled through the metering valve into the canister. Typically, in batches prepared for pharmaceutical use, each filled canister is check-weighed, coded with a batch number and packed into a tray for storage before release testing.

In an alternative process, an aliquot of the liquified formulation is added to an open canister under conditions which are sufficiently cold that the formulation does not vaporise, and then a metering valve crimped onto the canister.

In an alternative process an aliquot of medicament dissolved in the solubilising agent and any low-volatility component is dispensed into an empty canister, a metering valve is crimped on, and then the propellant is filled into the canister through the valve.

Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler for administration of the medicament into the lungs or nasal cavity of a patient. Suitable channelling devices comprise, for example a valve actuator and a cylindrical or cone-like passage through which medicament may be delivered from the filled canister via the metering valve to the nose or mouth of a patient eg. a mouthpiece actuator.

In a typical arrangement the valve stem is seated in a nozzle block which has an orifice leading to an expansion chamber. The expansion chamber has an exit orifice which extends into the mouthpiece. Actuator (exit) orifice diameters in the range 0.15–0.45 mm particularly 0.2–0.45 mm are generally suitable eg 0.15, 0.22, 0.25, 0.30, 0.33 or 0.42 mm. We have found that it is advantageous to use a small diameter eg 0.25 mm or less, particularly 0.22 mm since this tends to result in a higher FPM and lower throat deposition. 0.15 mm is also particularly suitable. The dimensions of the orifice should not be so small that blockage of the jet occurs.

Actuator jet lengths are typically in the range 0.30–1.7 mm eg 0.30, 0.65 or 1.50 mm. Smaller dimensions are preferred eg 0.65 mm or 0.30 mm.

Metered dose inhalers are designed to deliver a fixed unit dosage of medicament per actuation or 'puff', for example in the range of 25 to 250 µg medicament per puff.

Administration of medicament may be indicated for the treatment of mild, moderate or severe acute or chronic symptoms or for prophylactic treatment. Treatment may be of asthma, chronic obstructive pulmonary disease (COPD) or other respiratory disorder. It will be appreciated that the precise dose administered will depend upon the age and condition of the patient, the quantity and frequency of administration will ultimately be at the discretion of the attendant physician. Typically, administration may be one or more times, for example from 1 to 8 times per day, giving for example 1,2,3 or 4 puffs each time. The preferred treatment regime is 1 or 2 puffs of 25, 50, 125 or 250 µg/puff fluticasone propionate, 2 times per day.

The filled canisters and metered dose inhalers described herein comprise further aspects of the present invention.

A still further aspect of the present invention comprises a method of treating respiratory disorders such as, for example, asthma or chronic obstructive pulmonary disease (COPD), which comprises administration by inhalation of an effective amount of a formulation herein before described.

A further aspect of the present invention comprises the use of a formulation herein before described in the manufacture of a medicament for the treatment of respiratory disorders, eg. asthma or chronic obstructive pulmonary disease (COPD).

As mentioned above the advantages of the invention include the fact that formulations according to the invention may be more environmentally friendly, more stable, less susceptible to Oswald ripening or drug deposition onto internal surfaces of a metered dose inhaler, have better dosing uniformity, deliver a higher FPM, give lower throat deposition, be more easily or economically manufactured, or may be otherwise beneficial relative to known formulations.

The invention is illustrated with reference to the following examples:

EXAMPLE 1 AND 2

Formulations may be prepared with compositions as follows:

| Fluticasone propionate: | 0.1% w/v | 0.05% w/v |
| Ethanol: | 16% w/w | 7% |
| Glycerol: | 1.3% w/w | 1.3% |
| 1,1,1,2-tetrafluoroethane: | to 100% | to 100% |

These solution formulations may be filled into an aluminium canister under pressure and fitted with a metering valve having a 50 µl metering chamber.

These formulations are suitable for delivering 50 µg or 25 µg fluticasone propionate per actuation respectively.

EXAMPLE 3

Formulations were prepared with compositions as follows:

| | Form. 3a | Form. 3b | Form. 3c |
|---|---|---|---|
| Fluticasone propionate: | 0.1% w/v | 0.079% w/v | 0.05% w/v |
| Ethanol: | 21% w/w | 16% w/w | 10% |
| Glycerol: | 1.0% w/w | 1.0% w/w | 1.0% |
| 1,1,1,2-tetrafluoroethane: | to 100% | to 100% | to 100% |

These solution formulations were filled into aluminium canisters (120 actuations/canister; overage of 40 actuations) under pressure and fitted with a metering valve (Valois DF60) having metering chambers of volume 50 µl, 63 µl and 100 µl respectively.

These formulations are suitable for delivering 50 µg fluticasone propionate per actuation.

EXAMPLE 4

Formulations were prepared with compositions as follows:

| | Form. 4a | Form. 4b | Form. 4c |
|---|---|---|---|
| Fluticasone propionate: | 0.1% w/v | 0.079% w/v | 0.05% w/v |
| Ethanol: | 21% w/w | 16% w/w | 10% |
| 1,1,1,2-tetrafluoroethane: | to 100% | to 100% | to 100% |

These solution formulations were filled into aluminium canisters (120 actuations/canister; overage of 40 actuations) under pressure and fitted with a metering valve (Valois DF60) having metering chambers of volume 50 μl, 63 μl and 100 μl respectively.

These formulations are suitable for delivering 50 μg fluticasone propionate per actuation.

EXAMPLE 5

A formulation was prepared with compositions as follows:

| | |
|---|---|
| Fluticasone propionate: | 0.198% w/v |
| Ethanol: | 35% w/w |
| Glycerol: | 1.0% w/w |
| 1,1,1,2-tetrafluoroethane: | to 100% |

This solution formulation was filled into an aluminium canisters (120 actuations/canister; overage of 40 actuations) under pressure and fitted with a metering valve (Valois DF60) having metering chamber of volume 63 μl.

This formulation is suitable for delivering 125 μg fluticasone propionate per actuation.

EXAMPLE 6

A formulation was prepared with compositions as follows:

| | |
|---|---|
| Fluticasone propionate: | 0.198% w/v |
| Ethanol: | 35% w/w |
| 1,1,1,2-tetrafluoroethane: | to 100% |

This solution formulation was filled into an aluminium canisters (120 actuations/canister; overage of 40 actuations) under pressure and fitted with a metering valve (Valois DF60) having metering chamber of volume 63 μl.

This formulation is suitable for delivering 125 μg fluticasone propionate per actuation.

EXAMPLE 7

Formulations were prepared with compositions as follows:

| | Form. 7a | Form. 7b | Form. 7c |
|---|---|---|---|
| Fluticasone propionate: | 0.05% w/v | 0.05% w/v | 0.05% w/v |
| Ethanol: | 10% w/w | 10% w/w | 10% w/w |
| Glycerol: | 0.5% w/w | 2% w/w | 3% w/w |
| 1,1,1,2-tetrafluoroethane: | to 100% | to 100% | to 100% |

These solution formulations were filled into aluminium canisters (120 actuations/canister; overage of 40 actuations) under pressure and fitted with a metering valve (Valois DF60) having metering chamber of volume 100 μl.

These formulations are suitable for delivering 50 μg fluticasone propionate per actuation.

EXAMPLE 8

Formulations were prepared with compositions as follows:

| | | |
|---|---|---|
| Fluticasone propionate: | 0.025% w/v | 0.025% w/v |
| Ethanol: | 8% w/w | 7% w/w |
| Glycerol: | 1.0% w/w | 1.0% w/w |
| 1,1,1,2-tetrafluoroethane: | to 100% | to 100% |

These solution formulations were filled into an aluminium canisters (120 actuations/canister; overage of 40 actuations) under pressure and fitted with a metering valve (Valois DF60) having metering chamber of volume 100 μl.

These formulations are suitable for delivering 25 μg fluticasone propionate per actuation.

EXAMPLE 9

Formulations were prepared with compositions as follows:

| | |
|---|---|
| Formulation 9a: | |
| Fluticasone propionate: | 0.05% w/v |
| Dimethoxymethane: | 15% w/w |
| 1,1,1,2-tetrafluoroethane: | to 100% |
| Formulation 9b: | |
| Fluticasone propionate: | 0.05% w/v |
| Ethylacetate: | 15% w/w |
| 1,1,1,2-tetrafluoroethane: | to 100% |
| Formulation 9c: | |
| Fluticasone propionate: | 0.05% w/v |
| Dimethoxymethane: | 15% w/w |
| Glycerol: | 1% w/w |
| 1,1,1,2-tetrafluoroethane: | to 100% |
| Formulation 9d: | |
| Fluticasone propionate: | 0.05% w/v |
| Ethylacetate: | 15% w/w |
| Glycerol: | 1% w/w |
| 1,1,1,2-tetrafluoroethane: | to 100% |

These solution formulations were filled into aluminum canisters (120 actuations/canister; overage of 40 actuations) under pressure and fitted with a metering valve (Valois DF60) having metering chamber of volume 100 μl.

These formulations are suitable for delivering 50 μg fluticasone propionate per actuation.

EXAMPLE 10

Formulations were prepared with compositions as follows:

| | |
|---|---|
| Formulation 10a: | |
| Fluticasone propionate: | 0.05% w/v |
| Ethanol: | 10% w/w |
| Glycerol: | 1% w/w |
| 1,1,1,2-tetrafluoroethane: | to 100% |

-continued

Formulation 10b:

| | |
|---|---|
| Fluticasone propionate: | 0.05% w/v |
| Ethanol: | 10% w/w |
| PEG 200: | 1% w/w |
| 1,1,1,2-tetrafluoroethane: | to 100% |

Formulation 10c:

| | |
|---|---|
| Fluticasone propionate: | 0.05% w/v |
| Ethanol: | 10% w/w |
| PEG 400: | 1% w/w |
| 1,1,1,2-tetrafluoroethane: | to 100% |

Formulation 10d:

| | |
|---|---|
| Fluticasone propionate: | 0.05% w/v |
| Ethanol: | 10% w/w |
| Propylene glycol: | 1% w/w |
| 1,1,1,2-tetrafluoroethane: | to 100% |

Formulation 10e:

| | |
|---|---|
| Fluticasone propionate: | 0.05% w/v |
| Ethanol: | 18% w/w |
| 1,1,1,2,3,3,3-heptafluoro-n-propane: | to 100% |

Formulation 10f:

| | |
|---|---|
| Fluticasone propionate: | 0.05% w/v |
| Ethanol: | 18% w/w |
| Glycerol: | 1% w/w |
| 1,1,1,2,3,3,3-heptafluoro-n-propane: | to 100% |

Formulation 10g:

| | |
|---|---|
| Fluticasone propionate: | 0.025% w/v |
| Ethanol: | 14% w/w |
| 1,1,1,2,3,3,3-heptafluoro-n-propane: | to 100% |

Formulation 10h:

| | |
|---|---|
| Fluticasone propionate: | 0.025% w/v |
| Ethanol: | 14% w/w |
| Glycerol: | 1% w/w |
| 1,1,1,2,3,3,3-heptafluoro-n-propane: | to 100% |

Formulation 10i:

| | |
|---|---|
| Fluticasone propionate: | 0.025% w/v |
| Ethanol: | 7% w/w |
| 1,1,1,2-tetrafluoroethane: | to 100% |

Formulation 10j:

| | |
|---|---|
| Fluticasone propionate: | 0.025% w/v |
| Ethanol: | 7% w/w |
| Glycerol: | 1% w/w |
| 1,1,1,2-tetrafluoroethane: | to 100% |

These solution formulations were filled into aluminium canisters (120 actuations/canister; overage of 40 actuations) under pressure and fitted with a metering valve (Valois DF60) having metering chamber of volume 63 μl.

These formulations are suitable for delivering 31.5 μg (10a–10e) or 15.75 μg (10f, 10 g) fluticasone propionate per actuation. However the performance of these formulations is a model for formulations that would deliver 50 μg and 25 μg fluticasone propionate using a metering valve of 100 μl.

Andersen Cascade Impaction Data

Formulations as described in Examples 3, 4, 5 and 6 were profiled using an Andersen Cascade Impactor, using a 0.22 mm (orifice)×0.65 mm (jet length) actuator from Bespak (BK621 variant). Testing was performed on canisters at "beginning of use" (BoU) and delivered drug from 10 actuations was collected in the instrument after 4 priming actuations were fired to waste. Results are shown in Tables 1–4 and FIGS. 1–4 and 11. For comparison, data from a Flixotide Evohaler (trademark) (particulate fluticasone propionate suspended in HFA134a (excipient free) 50 μg per actuation) product is also shown in some figures.

The 0.079% w/v fluticasone propionate products of Examples 3 and 4 (50 μg per actuation; 63 μl metering chamber) were profiled using an Andersen Cascade Impactor in a study to see the effect of actuator orifice diameter and length.

Three actuators were used:
0.50 mm diameter orifice×1.50 mm jet length
0.33 mm diameter orifice×1.50 mm jet length
0.22 mm diameter orifice×0.65 mm jet length Results are shown in Table 5 and FIGS. 5 to 9. For comparison, data from a Flixotide Evohaler (trademark) (particulate fluticasone propionate suspended in HFA134a (excipient free) 50 μg per actuation) product is also shown in some figures.

The results show the best performance (as indicated by highest FPM) in products containing a relatively low concentration of ethanol (say around 10%) and containing glycerol (say around 1%). A small actuator orifice diameter (say around 0.22 mm) is also seen to be preferred.

The solubility of fluticasone propionate in ethanol in the presence of HFA134a is shown in FIG. 10.

A study was performed on the 0.05% w/v fluticasone propionate formulations (HFA134a/10% ethanol) of Examples 3 (Formulation 3c), 4 (Formulation 4c) and 7 (Formulations 7a, 7b and 7c) with a 0.22 mm×0.65 mm actuator using an Andersen Cascade Impactor to consider the effect of glycerol content on the following properties: (i) MMAD, (ii) throat deposition, and (iii) stage 3–7 deposition. The results are shown in FIGS. 12–14. For maximum deposition in the desired region without excessive throat deposition the optimal glycerol concentration appears to be around 0.8–1.6% w/w, particularly 1.0–1.6% w/w.

A study was performed using an Andersen Cascade Impactor to compare the properties of formulations containing different solubilising agents. An actuator of dimensions 0.22 mm×0.65 mm was used for the study. The results of the analysis of the formulations of Example 9 Formulations 9a, 9b, 9c and 9d and a comparison with the formulations of Example 3 Formulation 3c and Example 4 Formulation 4c are shown in Table 6 and FIG. 15. The ethanol with glycerol profile clearly appears the most attractive since it demonstrates the highest FPM content in view of the high dosing in stages 4 and 4 relative to the other profiles. Nevertheless the methylal profiles also looked of significant interest in view of the very low throat deposition. The addition of 1% glycerol shifted the methylal profile to lower stages only to a small extent, perhaps in view of its greater volatility than ethanol. A higher percentage of glycerol would be expected to increase the magnitude of the shift.

A study was performed using an Andersen Cascade Impactor to compare the properties of formulations containing different low volatility components. An actuator of dimensions 0.22 mm×0.65 mm was used for the study. The results of the analysis of the formulations of Example 10 Formulations 10a to 10d are shown in Table 7 and FIG. 16. Particularly good profiles are shown by glycerol and PEG400 which demonstrate relatively low throat deposition and high dosing in stages 4 and 5.

A study was performed using an Andersen Cascade Impactor to study the properties of 0.05% fluticasone propionate formulations containing 1,1,1,2,3,3,3-heptafluoro-n-propane (HFA227) as propellant. An actuator of dimensions 0.22 mm×0.65 mm was used for the study. The results of the analysis of the formulations of Example 10 Formulations 10e and 10f are shown in Table 8 and FIG. 17. Comparison with the HFA134a aerosol formulation of Formulation 10a is shown.

A study was performed using an Andersen Cascade Impactor to study the properties of 0.025% fluticasone propionate formulations containing 1,1,1,2-tetrafluoroethane (HFA134a) or 1,1,1,2,3,3,3-heptafluoro-n-propane (HFA227) as propellant. An actuator of dimensions 0.22 mm×0.65 mm was used for the study. The results of the analysis of the formulations of Example 10 Formulations 10g to 10j are shown in Table 9 and FIGS. 18 and 19. The HFA134a product with ethanol shows a particularly attractive profile eg as shown by a high total delivered dose and a relatively low throat deposition.

BRIEF DESCRIPTION OF THE DRAWINGS

Table 1: Effect of valve on FPM in fluticasone propionate HFA134a solution aerosols (50 µg/actuation)

Table 2: Effect of different levels of ethanol on FPM in fluticasone propionate/HFA134a solution aerosols Table 3: Effect of different levels of ethanol on FPM in fluticasone propionate/HFA134a solution aerosols (valve size effect ignored)

Table 4: Cascade impaction analysis of fluticasone propionate/HFA134a solution aerosols (125 µg/actuation) containing 35% ethanol or 35% ethanol and 1% glycerol Table 5: Cascade impaction analysis of fluticasone propionate/HFA134a solution aerosols (50 µg/actuation) containing 16% ethanol or 16% ethanol and 1% glycerol Table 6: Cascade impaction analysis of fluticasone propionate/HFA134a solution aerosols (50 µg/actuation) containing various solubiling agents with and without 1% glycerol Table 7: Cascade impaction analysis of fluticasone propionate/HFA134a solution aerosols (50 µg/actuation) containing various low volatility components Table 8: Cascade impaction analysis of fluticasone propionate solution aerosols (50 µg/actuation) containing various propellants Table 9: Cascade impaction analysis of fluticasone propionate solution aerosols (25 µg/actuation) containing various propellants

FIG. 10: Solubility of fluticasone propionate in ethanol/HFA134a.

FIG. 15: Cascade impaction analysis of fluticasone propionate/HFA134a solution aerosols (50 µg/actuation) containing ethanol, methylal or ethylacetate as solubilising agent, with and without 1% glycerol FIG. 18: Cascade impaction analysis of fluticasone propionate in HFA227 or HFA134a solution aerosols (25 µg actuation) containing ethanol

Figure 1:
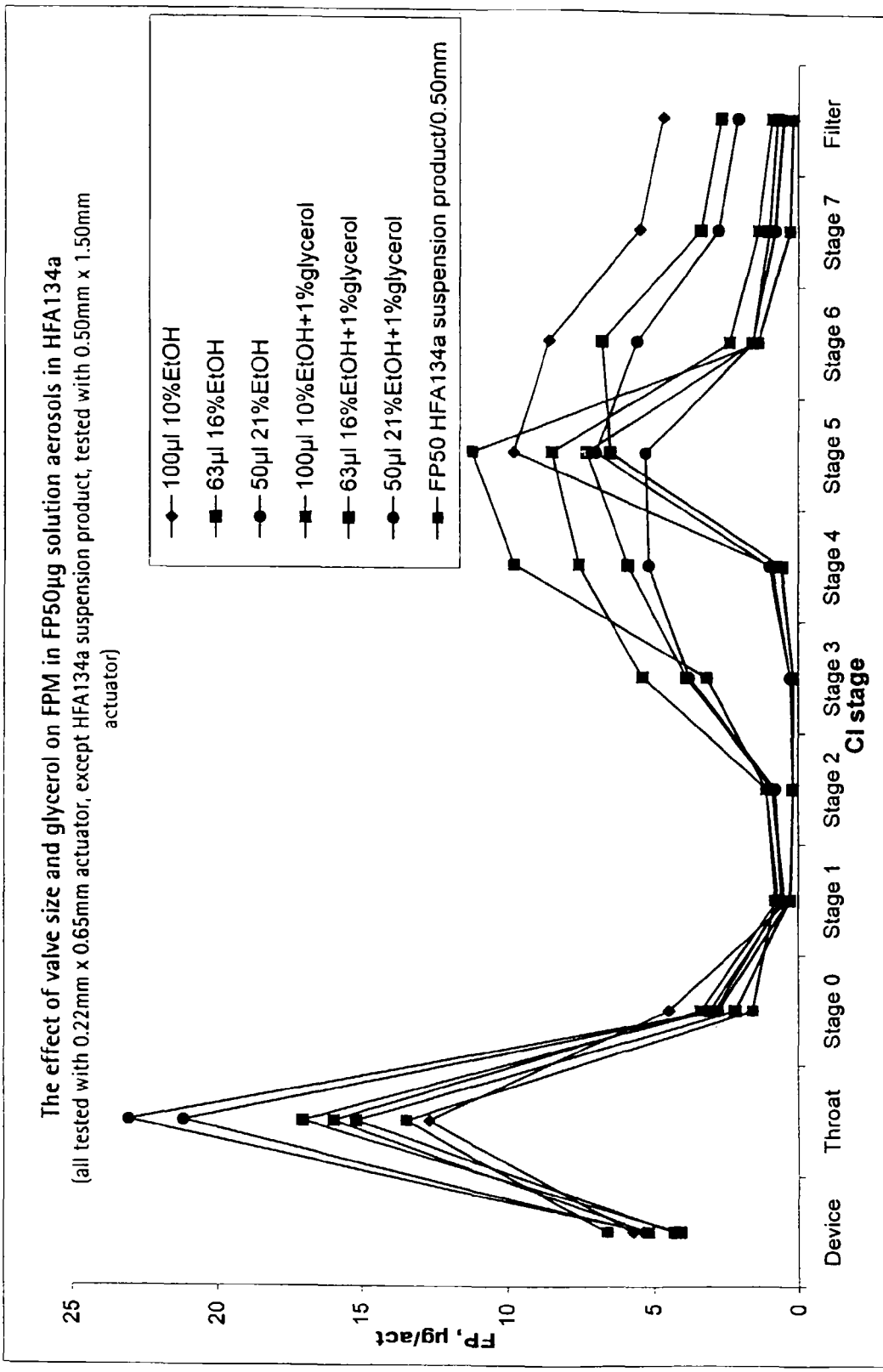
FIG. 1: Effect of valve size and glycerol on FPM in fluticasone propionate solution aerosols in HFA134a (50 µg/actuation)
Figure 2:
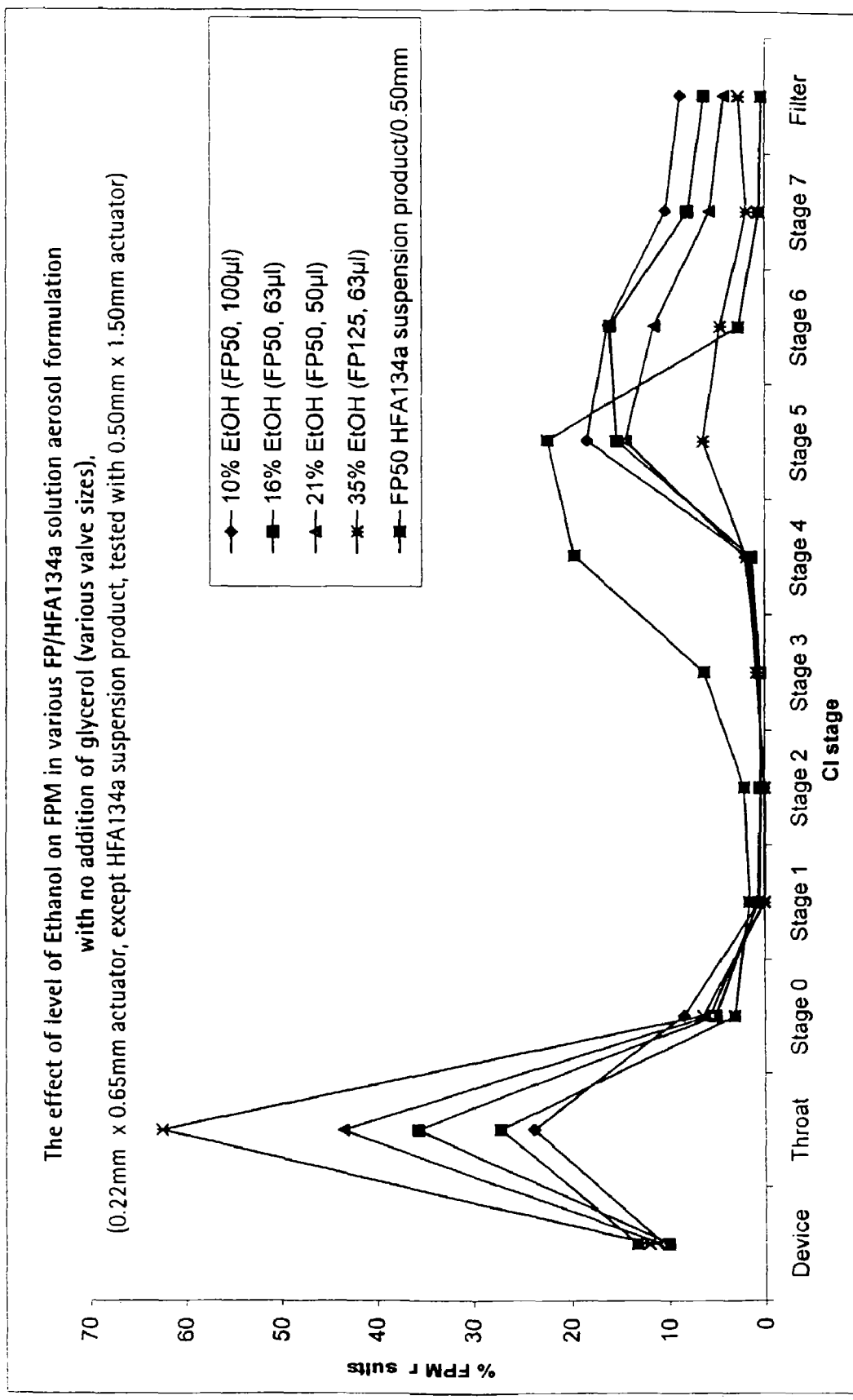
FIG. 2: Effect of level of ethanol on FPM in various fluticasone propionate/HFA134a solution aerosols with no addition of glycerol
Figure 3:
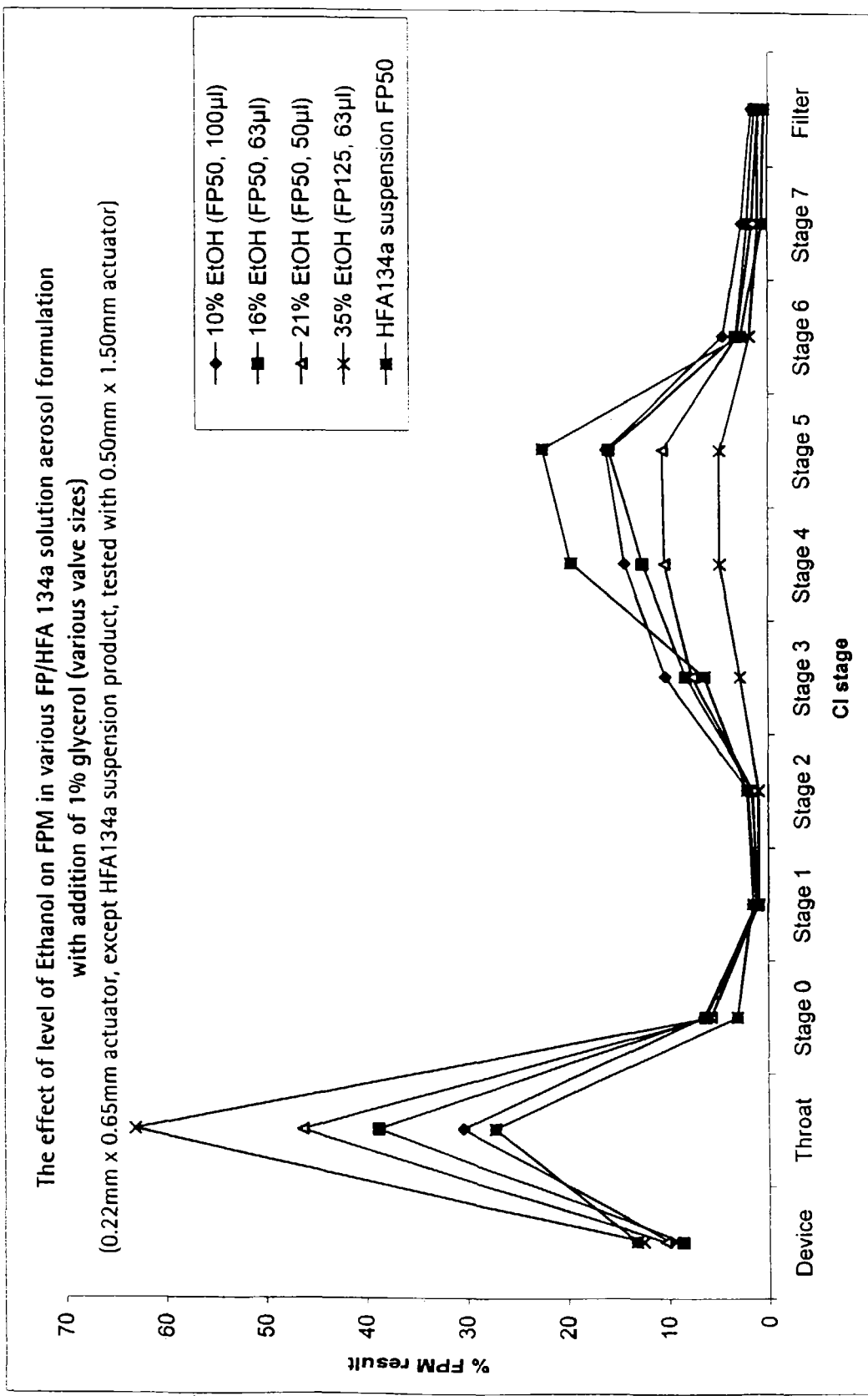
FIG. 3: Effect of level of ethanol on FPM in various fluticasone propionate/HFA134a solution aerosols with addition of 1% glycerol
Figure 4:
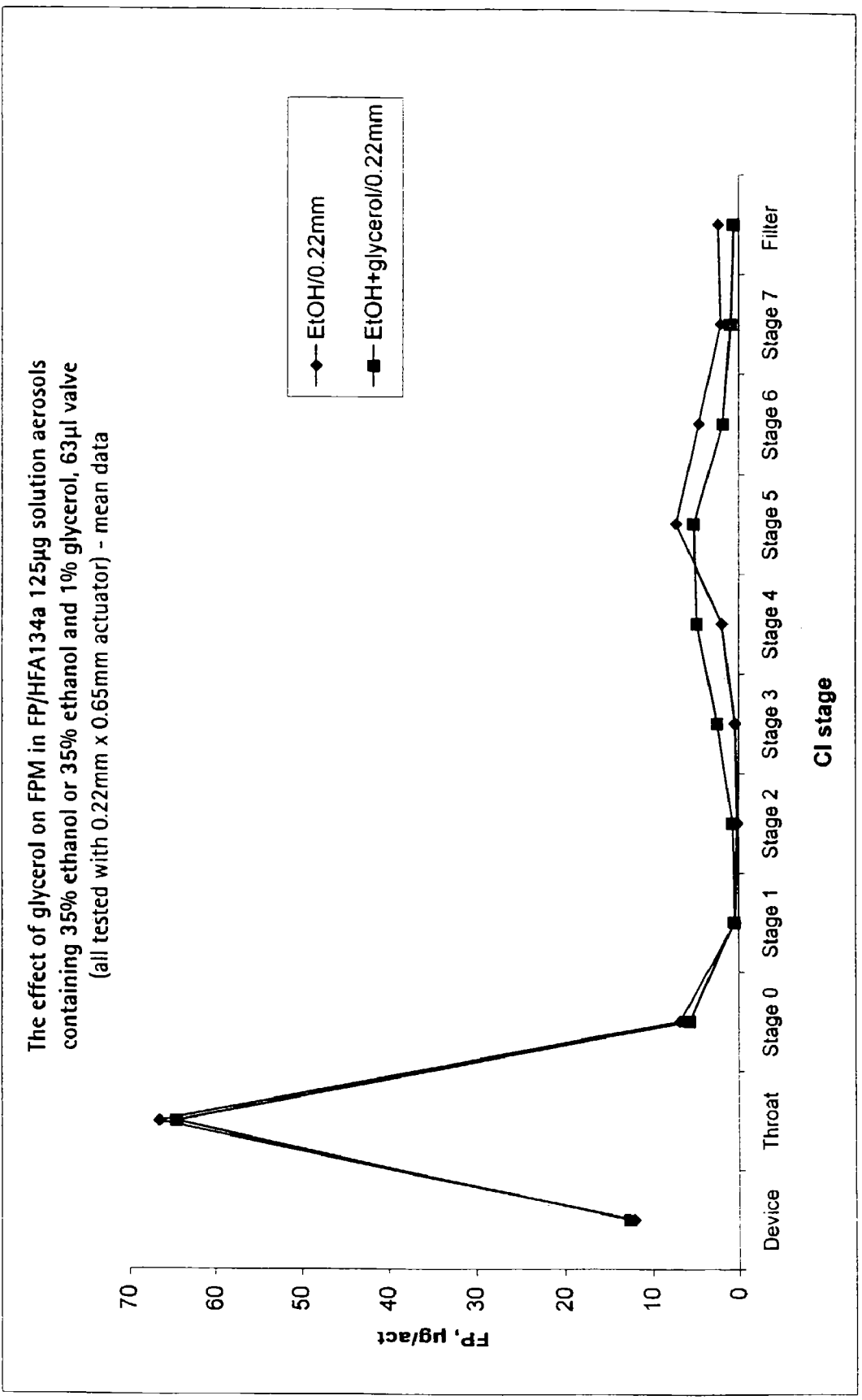
FIG. 4: Effect of glycerol on FPM in fluticasone propionate 125 µg/HFA134a solution aerosols containing 35% ethanol or 35% ethanol and 1% glycerol
Figure 5:
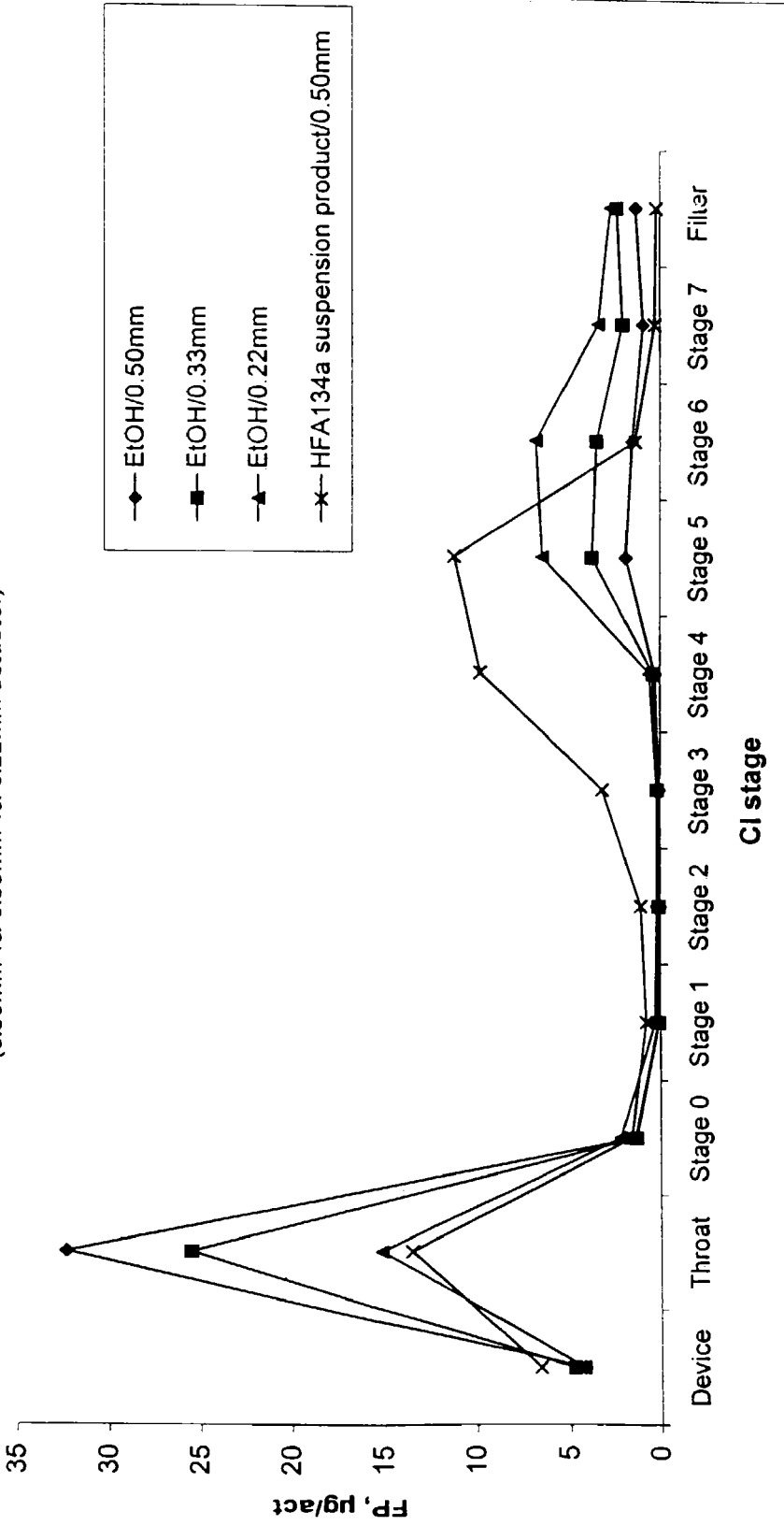
FIG. 5: Effect of actuator dimensions on FPM and throat in fluticasone propionate/HFA134a solution aerosols (50 µg/actuation) containing 16% ethanol
Figure 6:
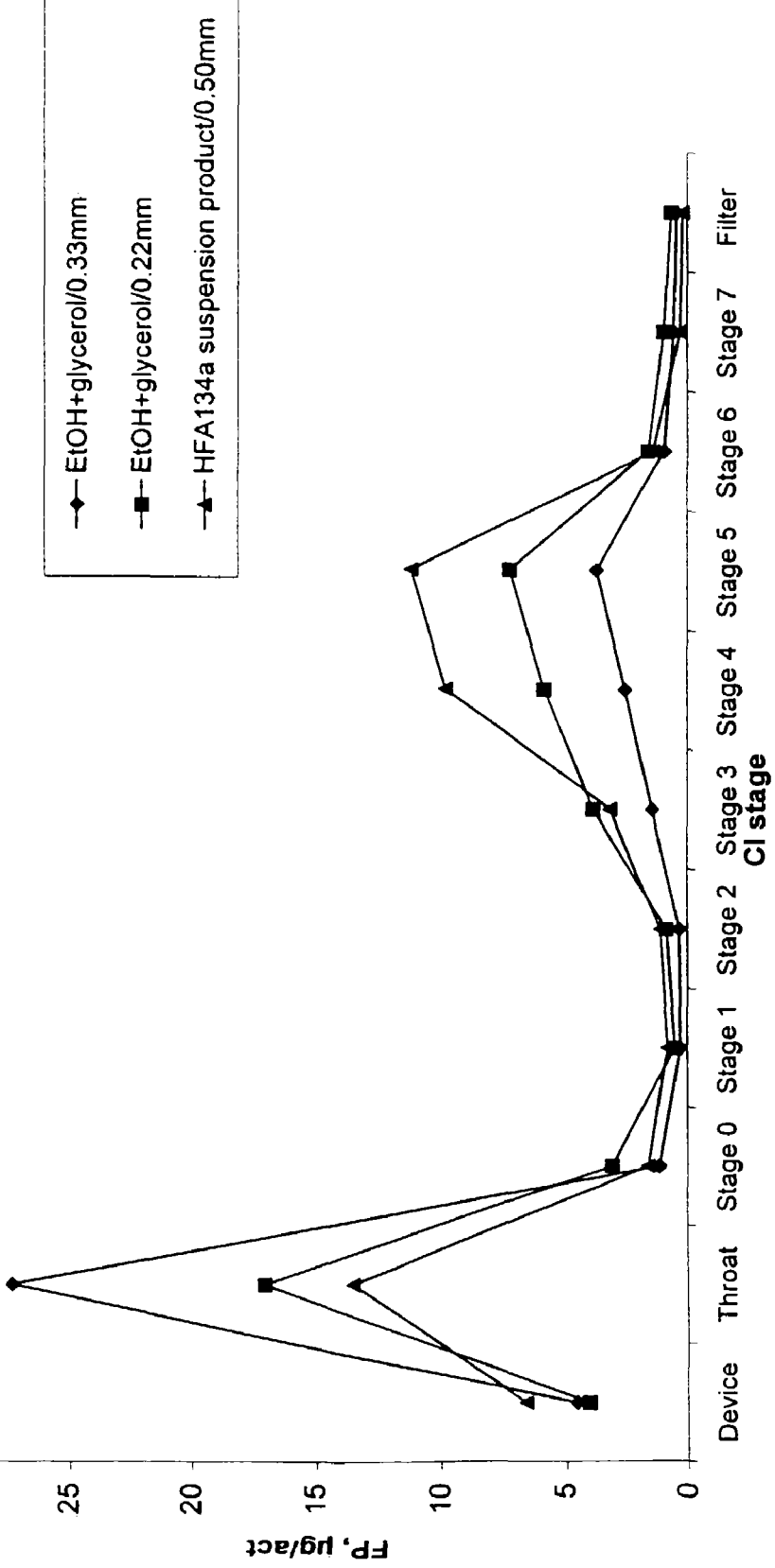
FIG. 6: Effect of actuator dimensions on FPM and throat in fluticasone propionate/HFA134a solution aerosols (50 µg/actuation) containing 16% ethanol and 1% ethanol
Figure 7:
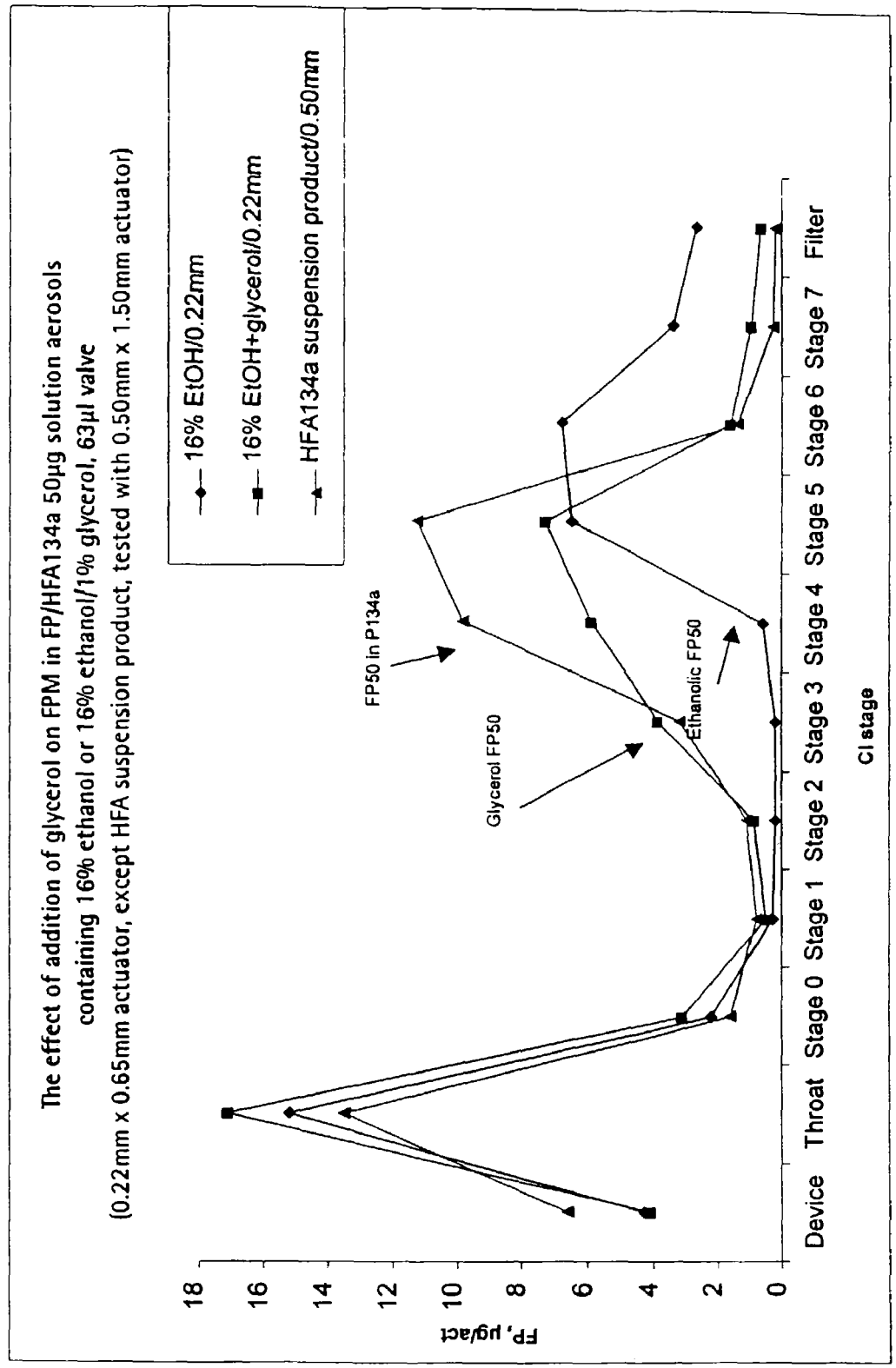
FIG. 7: The effect of addition of glycerol on FPM in fluticasone propionate 50 µg/HFA134a solution aerosols containing 16% ethanol or 16% ethanol and 1% glycerol (0.22 mm diameter actuator orifice)
Figure 8:
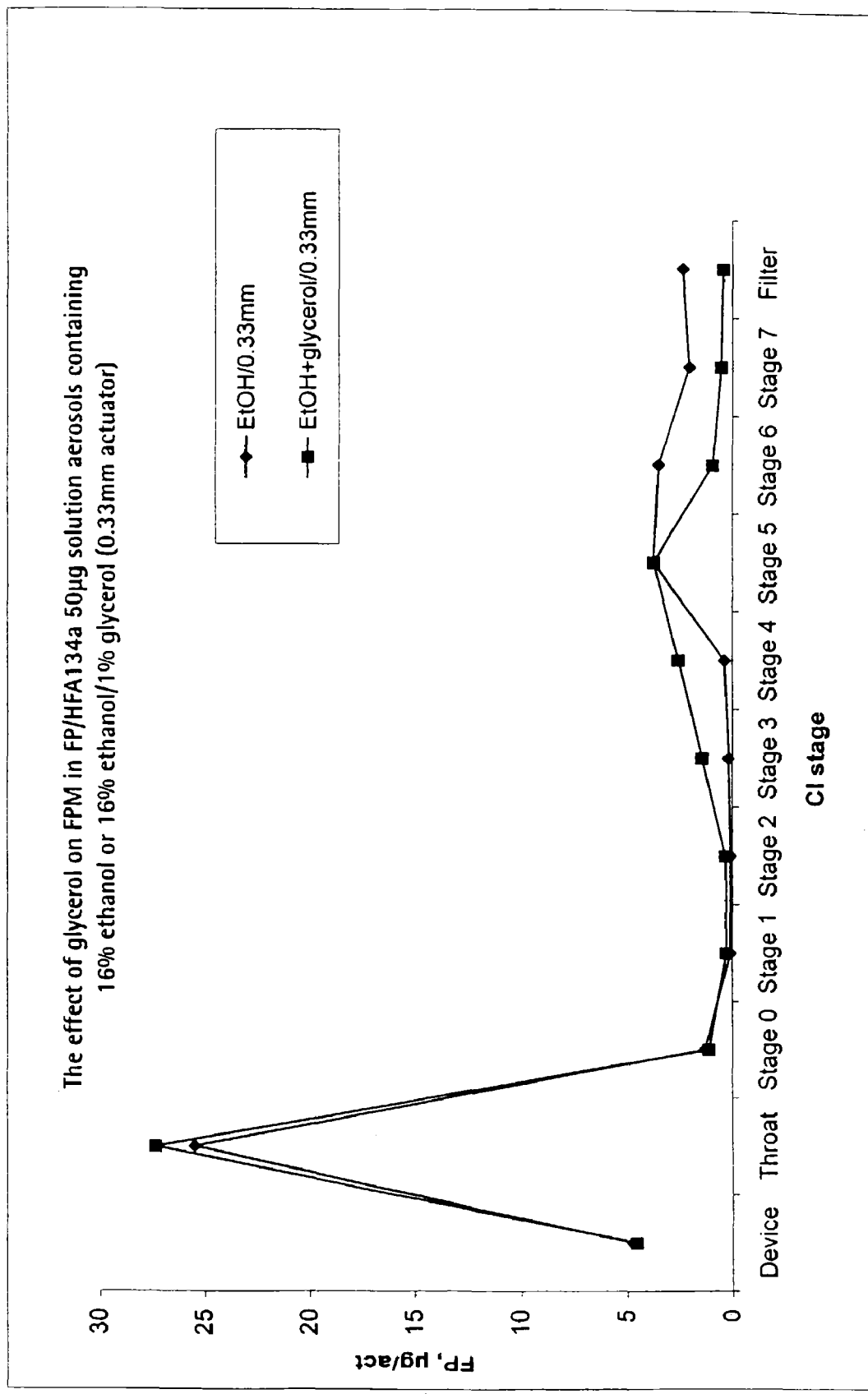
FIG. 8: The effect of addition of glycerol on FPM in fluticasone propionate 50 µg/HFA134a solution aerosols containing 16% ethanol or 16% ethanol and 1% glycerol (0.33 mm diameter actuator orifice)
Figure 9:
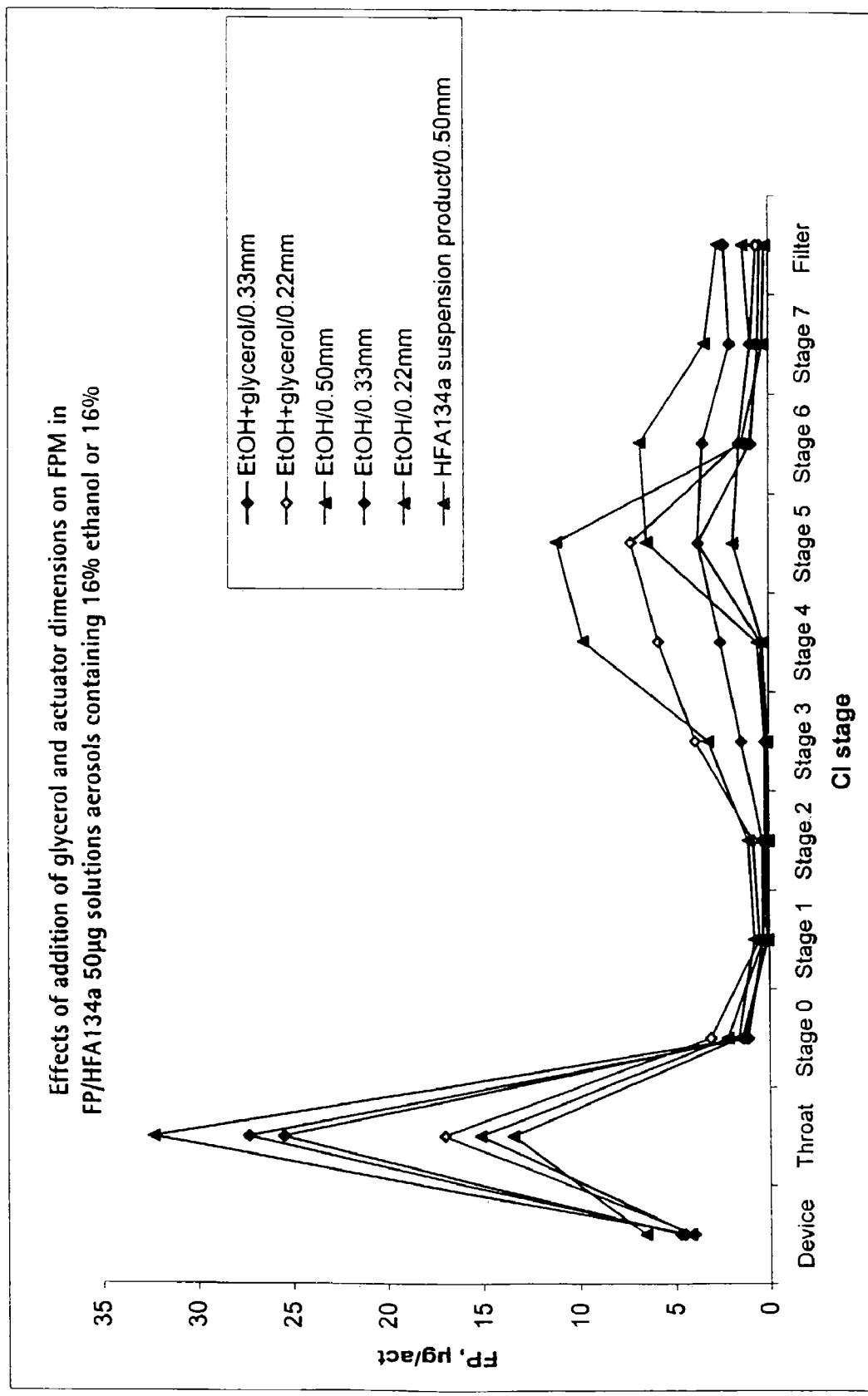
FIG. 9: Effects of addition of glycerol and actuator dimensions on FPM in fluticasone propionate 50 µg/HFA134a solution aerosols containing 16% ethanol or 16% ethanol and 1% glycerol (all actuator variants)
Figure 10:
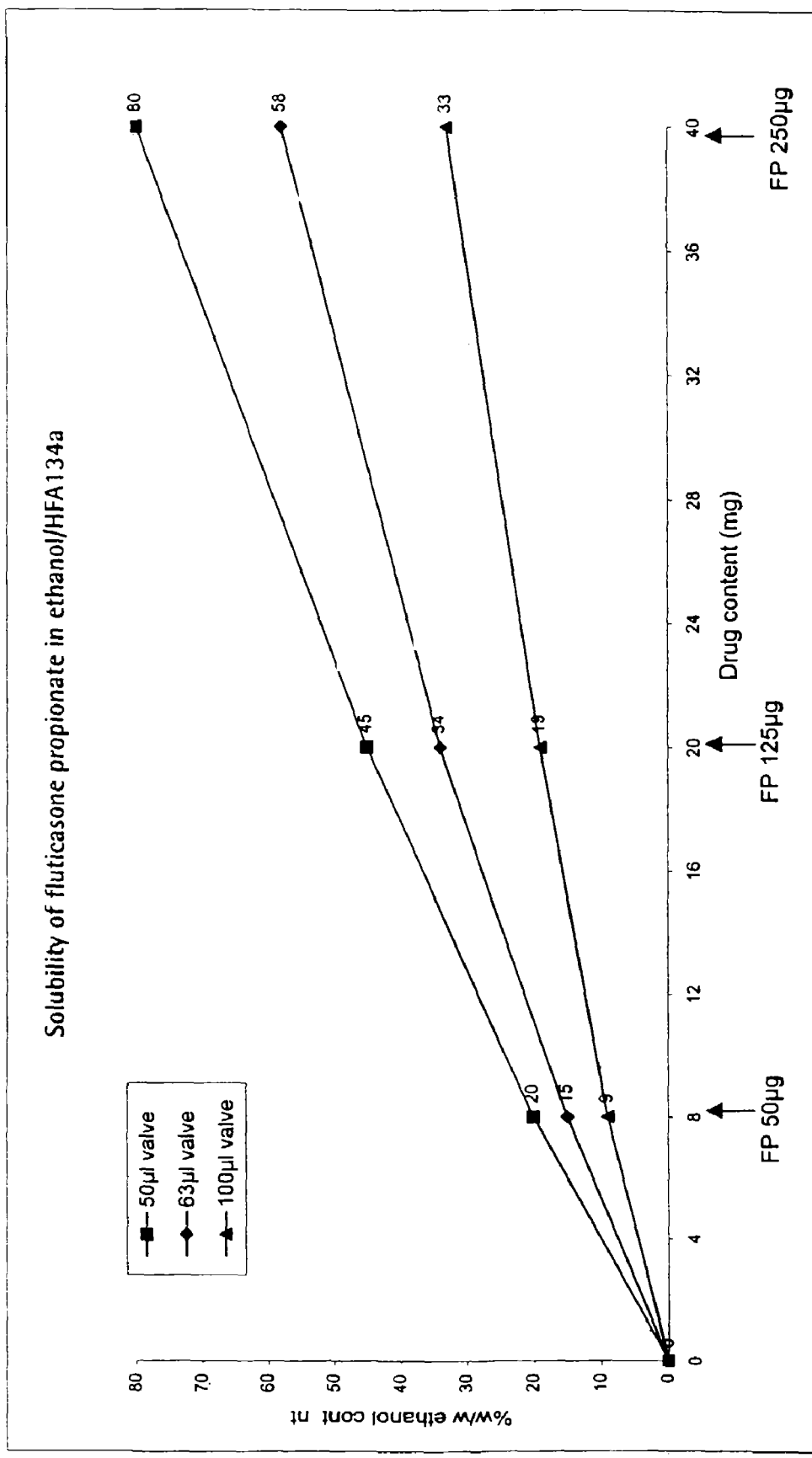
Figure 11:
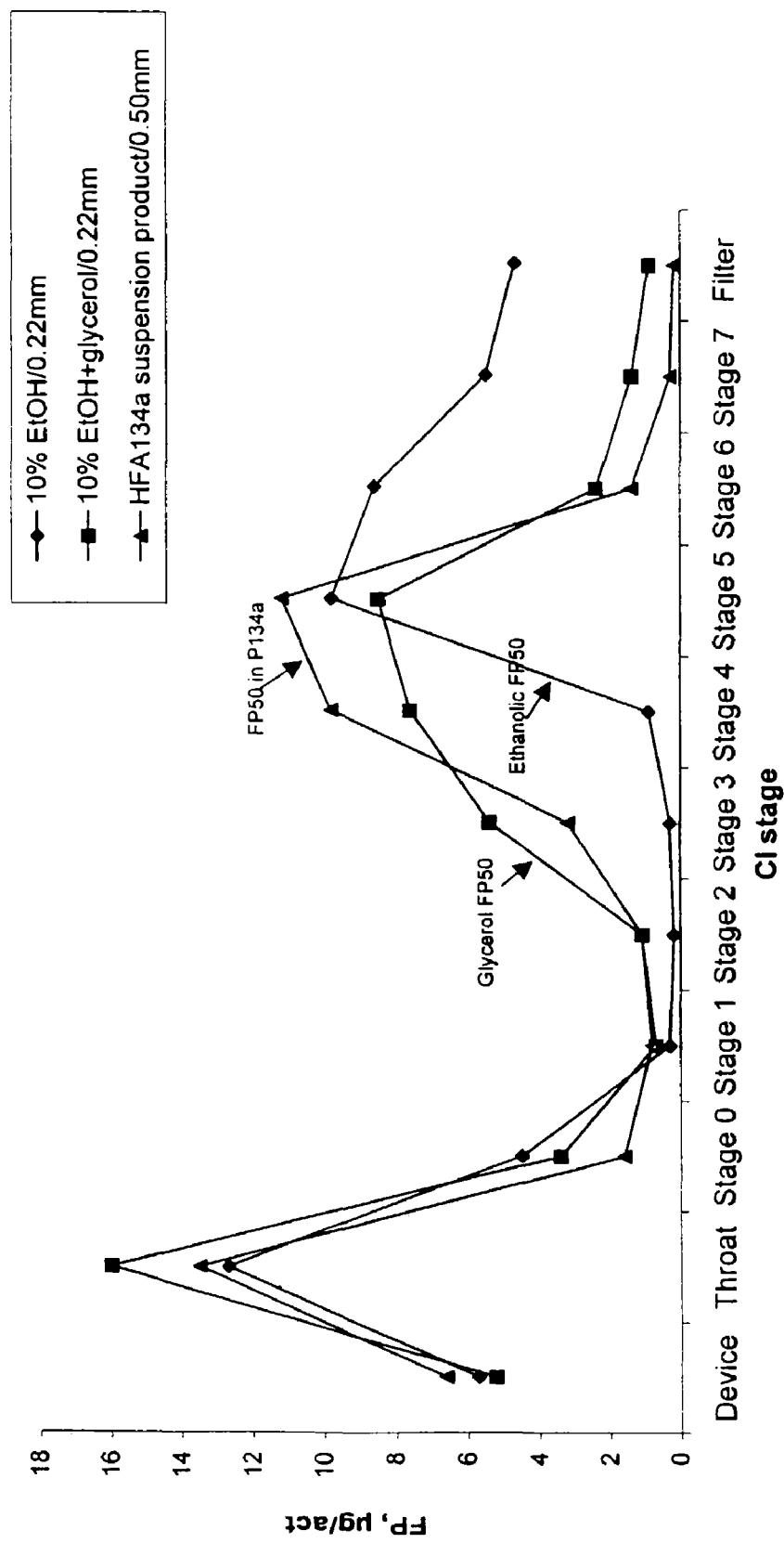
FIG. 11: Effects of addition of glycerol and actuator dimensions on FPM in fluticasone propionate 50 µg/HFA134a solution aerosols containing 10% ethanol or 10% ethanol and 1% glycerol
Figure 12:
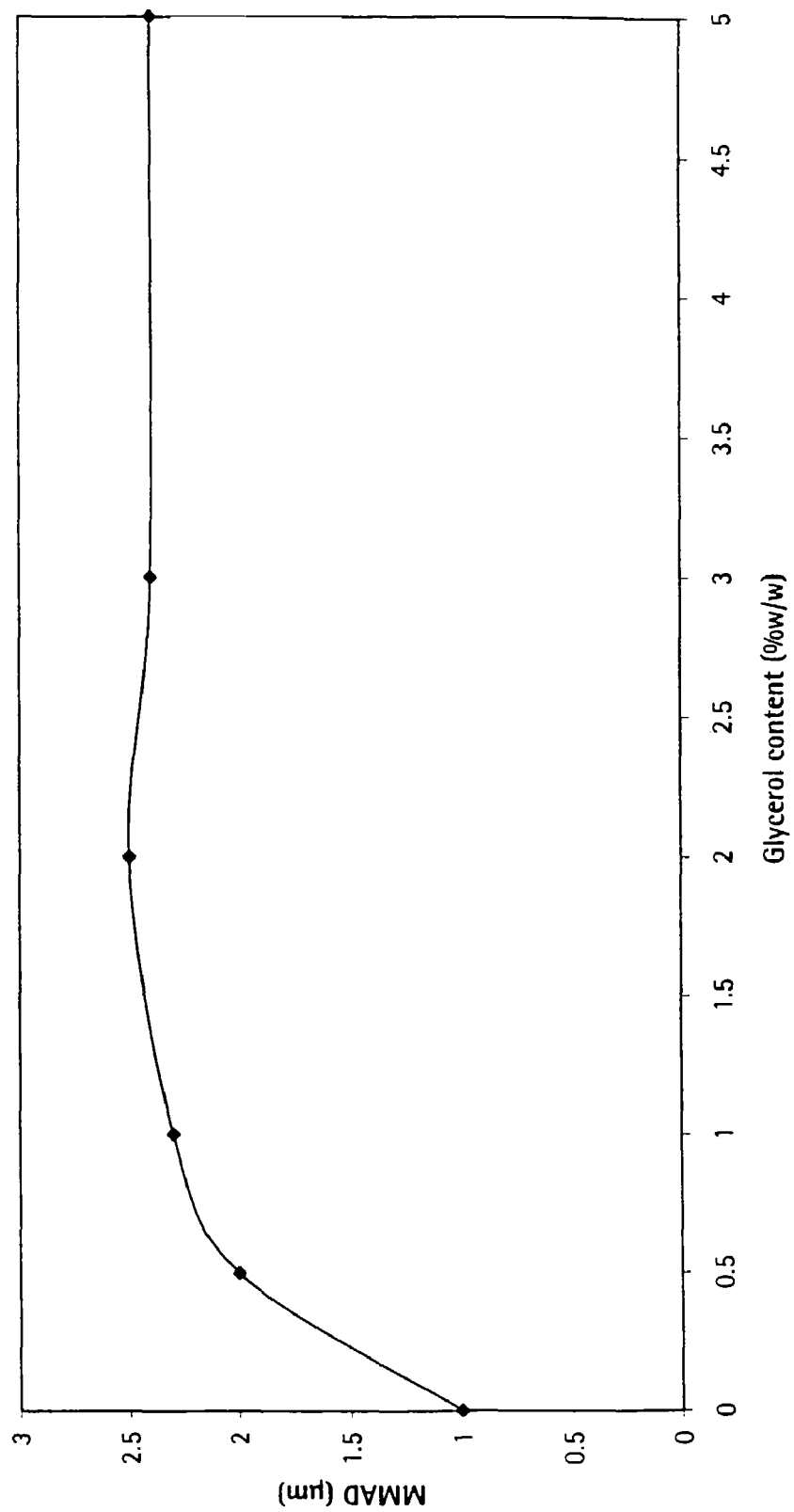
FIG. 12: Effects of addition of glycerol on MMAD in fluticasone propionate 50 µg/HFA134a solution aerosols containing 10% ethanol
Figure 13:
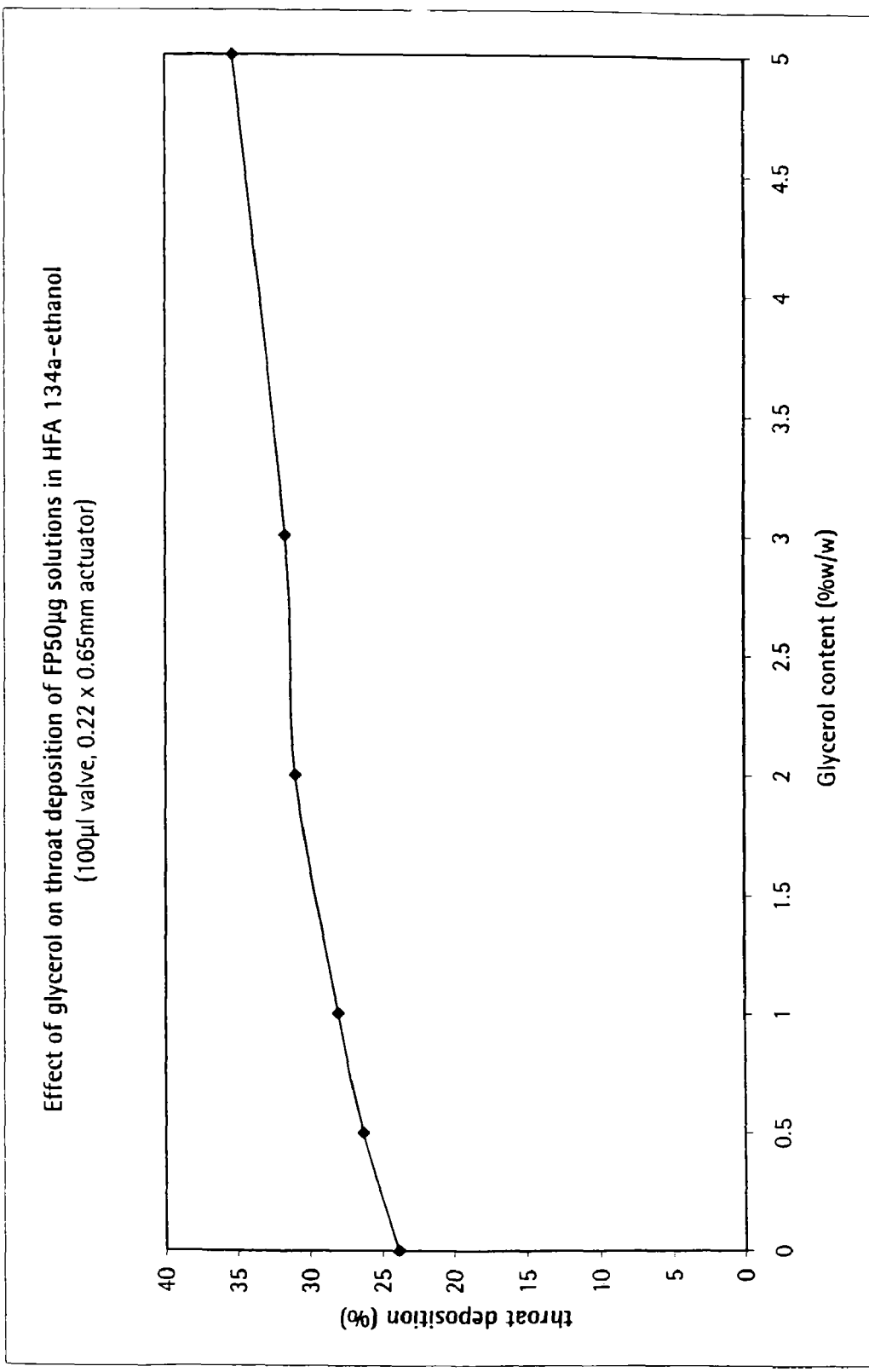
FIG. 13: Effects of addition of glycerol on throat deposition in fluticasone propionat 50 µg/HFA134a solution aerosols containing 10% ethanol
Figure 14:
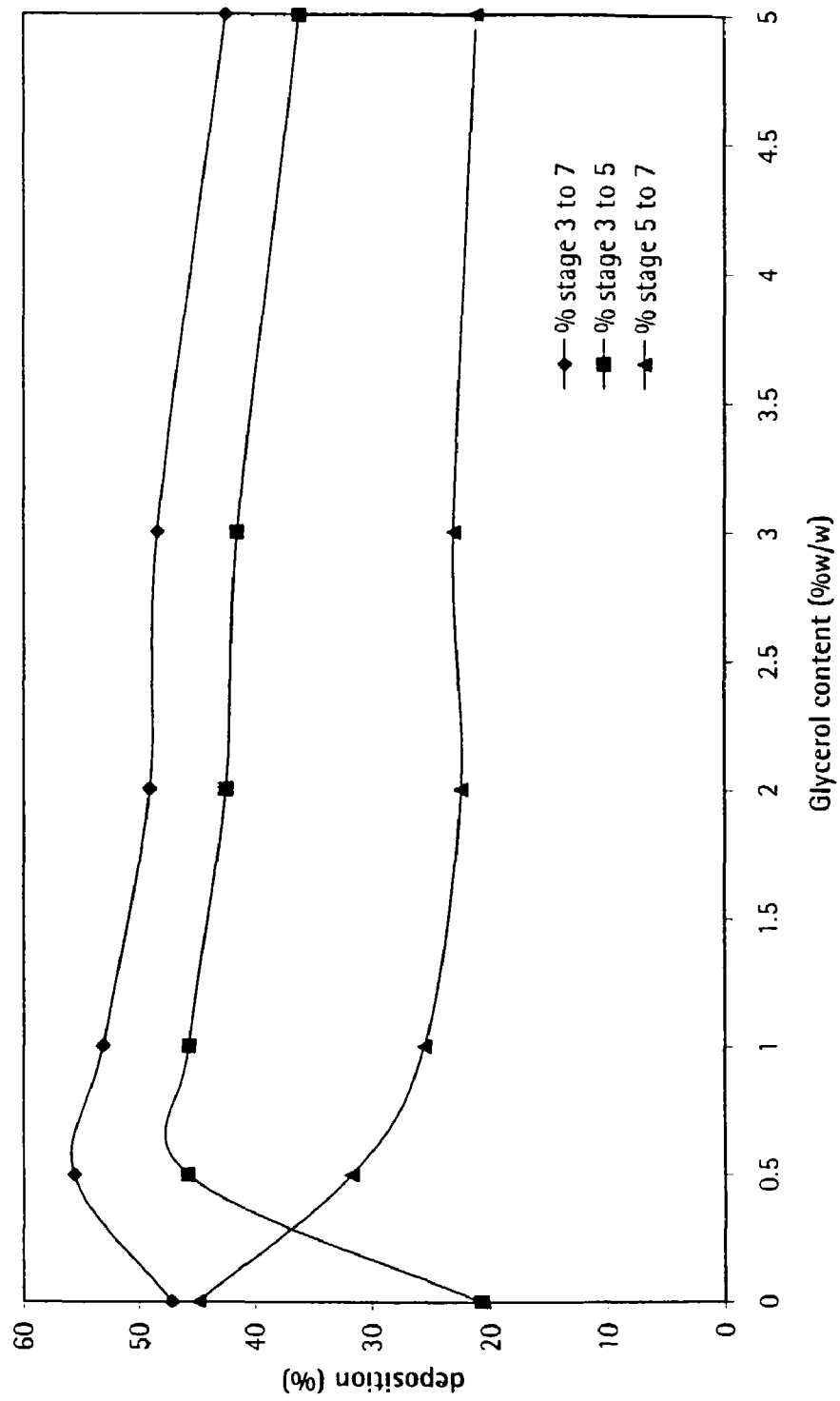
FIG. 14: Effects of addition of glycerol on stage 3–7 deposition in fluticasone propionate 50 µg/HFA134a solution aerosols containing 10% ethanol
Figure 16:
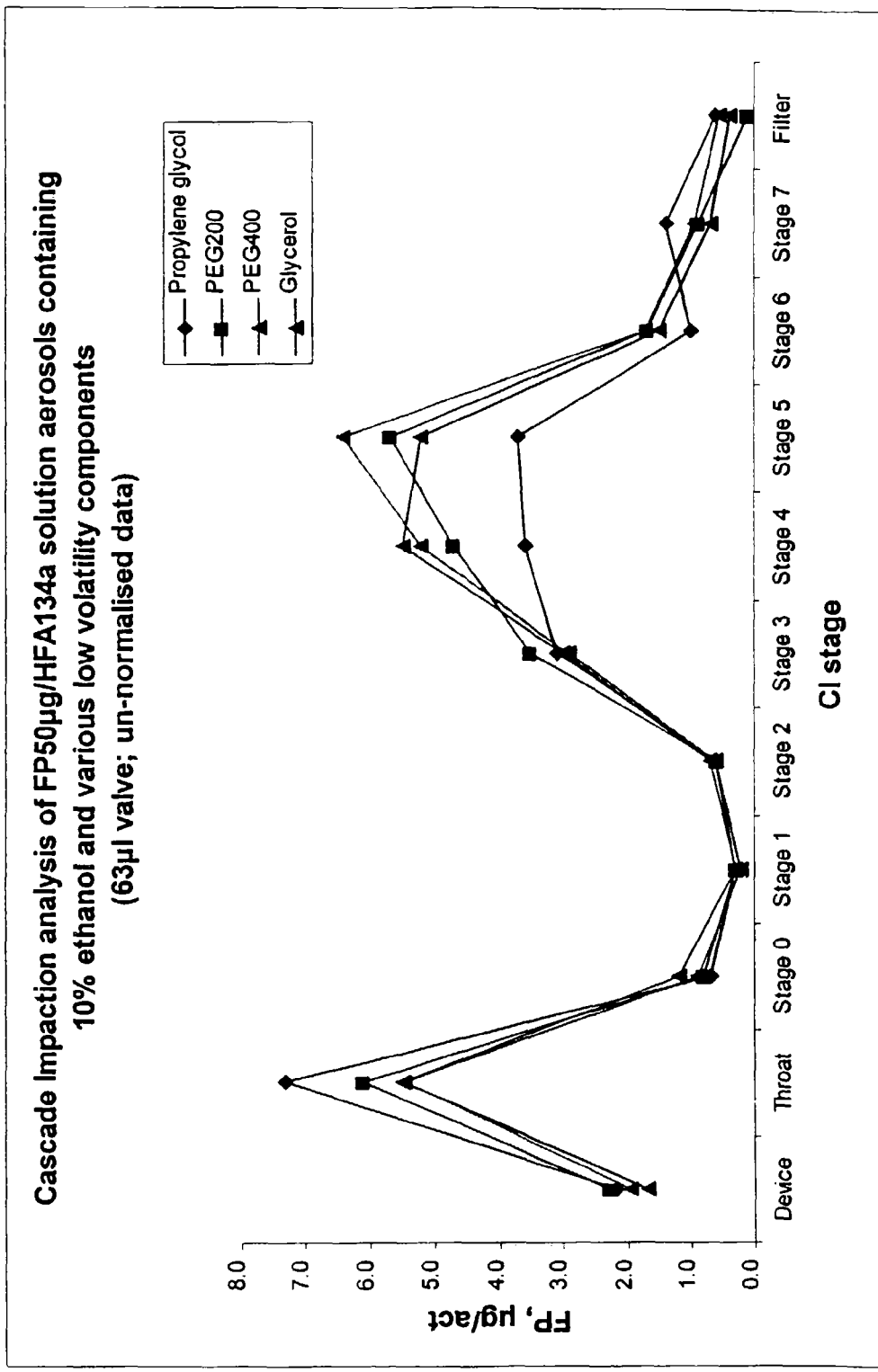
FIG. 16: Cascade impaction analysis of fluticasone propionate/HFA134a solution aerosols (50 µg/actuation) containing various low volatility components and 10% ethanol
Figure 17:
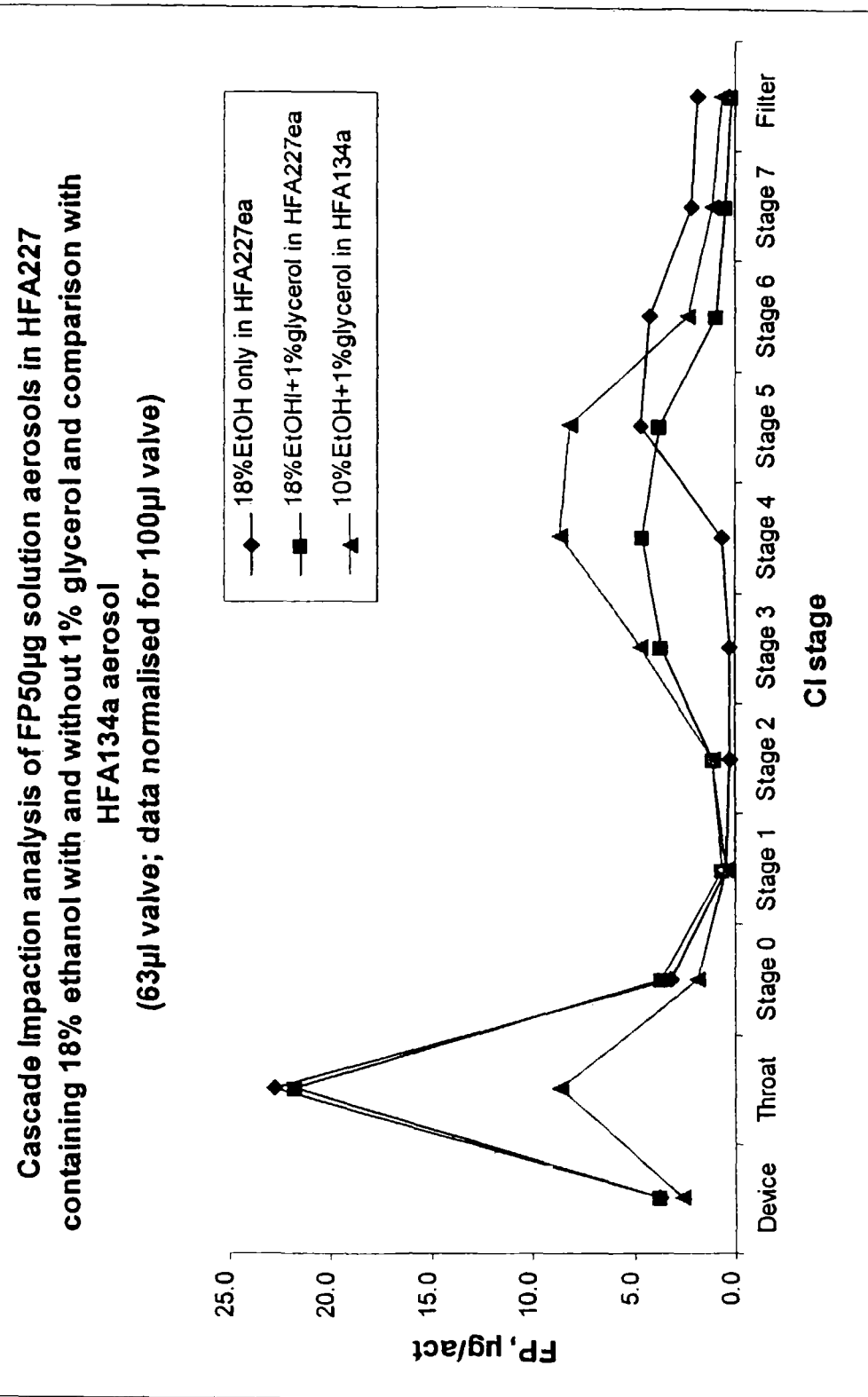
FIG. 17: Cascade impaction analysis of fluticasone propionate/HFA227 solution aerosols (50 µg actuation) containing 18% ethanol with and without 1% glycerol and comparison with HFA134a aerosol
Figure 19:
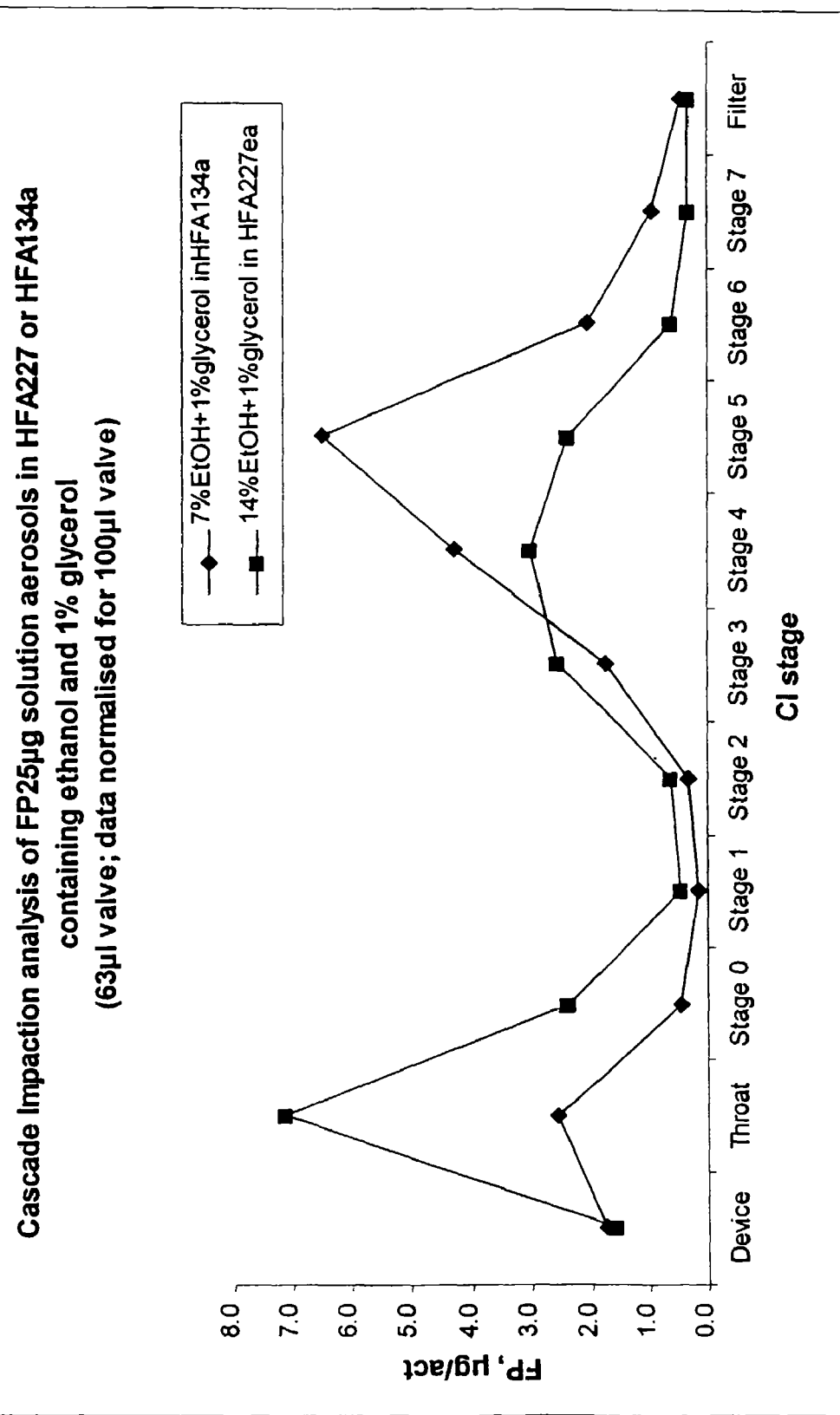
FIG. 19: Cascade impaction analysis of fluticasone propionate in HFA227 or HFA134a solution aerosols (25 µg actuation) containing ethanol and 1% glycerol Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

Above mentioned patents and patent applications are hereinbefore incorporated by reference.

| Abbreviations | |
|---|---|
| FPM | fine particle mass |
| FP | fluticasone propionate |
| m/c | metering chamber |
| BoU | beginning of use |
| PEG | polyethyleneglycol |
| Form. | Formulation |
| MMAD | mass median aerodynamic diameter |

TABLE 1

The effect of valve on FPM in FP50 μg solution aerosols
All data generated with 0.22 mm actuator, except HFA134a suspension product
tested with 0.50 mm actuator
μg Results Cascade Impaction

| Formulation | Ethanol only | | | Ethanol and 1% glycerol | | | HFA134a* |
|---|---|---|---|---|---|---|---|
| Ethanol conc. | 10% w/w | 16% w/w | 21% w/w | 10% w/w | 16% w/w | 21% w/w | — |
| Valve size | 100 μl | 63 μl | 50 μl | 100 μl | 63 μl | 50 μl | 50 μl |
| Product | FP | FP | FP | FP | FP | FP | FP |
| Product strength | 50 μg | 50 μg | 50 μg | 50 μg | 50 μg | 50 μg | 50 μg |
| Device | 5.7 | 4.3 | 5.3 | 5.2 | 4.1 | 5.2 | 6.6 |
| Throat | 12.7 | 15.2 | 21.2 | 16.0 | 17.1 | 23.1 | 13.5 |
| Stage 0 | 4.5 | 2.2 | 2.8 | 3.4 | 3.1 | 2.9 | 1.6 |
| Stage 1 | 0.3 | 0.3 | 0.3 | 0.7 | 0.5 | 0.6 | 0.8 |
| Stage 2 | 0.2 | 0.2 | 0.2 | 1.1 | 0.9 | 0.8 | 1.1 |
| Stage 3 | 0.3 | 0.2 | 0.3 | 5.4 | 3.9 | 3.8 | 3.2 |
| Stage 4 | 0.9 | 0.6 | 1.0 | 7.6 | 5.9 | 5.2 | 9.8 |
| Stage 5 | 9.8 | 6.5 | 7.0 | 8.5 | 7.3 | 5.3 | 11.2 |
| Stage 6 | 8.6 | 6.8 | 5.6 | 2.4 | 1.6 | 1.6 | 1.4 |
| Stage 7 | 5.5 | 3.4 | 2.8 | 1.4 | 1.0 | 0.8 | 0.3 |
| Filter | 4.7 | 2.7 | 2.1 | 0.9 | 0.7 | 0.5 | 0.2 |
| Total | 53.2 | 42.4 | 48.6 | 52.6 | 46.1 | 49.8 | 48.0 |
| Total ex-device | 47.5 | 38.1 | 43.3 | 47.4 | 42.0 | 44.6 | 43.3 |
| FPM, St3 + St4 + St5 | 11.0 | 7.3 | 8.3 | 21.5 | 17.1 | 14.3 | 15.7 |
| FPM, St5 + St6 + St7 | 23.9 | 16.7 | 15.4 | 12.3 | 9.9 | 7.7 | 8.8 |

*Flixotide Evohaler suspension formulation

TABLE 2

Effect of different levels of Ethanol on FPM
in FP/HFA134a solution aerosols
All fitted with 63 μl m/c and tested with
0.22 mm actuator
% Results Cascade Impaction

| Formulation | Ethanol only | | Ethanol and 1% glycerol | |
|---|---|---|---|---|
| Ethanol conc. | 16% w/w | 35% w/w | 16% w/w | 35% w/w |
| Valve size | 63 μl | 63 μl | 63 μl | 63 μl |
| Product | FP | FP | FP | FP |
| Product strength | 50 μg | 125 μg | 50 μg | 125 μg |
| Device | 10.1 | 12.1 | 8.6 | 12.6 |
| Throat | 35.8 | 62.6 | 38.8 | 63.1 |
| Stage 0 | 5.2 | 6.5 | 6.3 | 5.8 |
| Stage 1 | 0.7 | 0.0 | 1.0 | 1.0 |
| Stage 2 | 0.5 | 0.0 | 1.7 | 1.0 |
| Stage 3 | 0.5 | 0.9 | 8.2 | 2.9 |
| Stage 4 | 1.4 | 1.9 | 12.6 | 4.9 |
| Stage 5 | 15.3 | 6.5 | 15.9 | 4.9 |
| Stage 6 | 16.0 | 4.7 | 3.3 | 1.9 |
| Stage 7 | 8.0 | 1.9 | 2.1 | 1.0 |
| Filter | 6.4 | 2.8 | 1.4 | 1.0 |
| Total | 100.0 | 100.0 | 100.0 | 100.0 |
| Total ex-device | 89.9 | 87.9 | 91.4 | 87.4 |
| FPM, St3 + St4 + St5 | 17.2 | 9.3 | 36.7 | 12.6 |
| FPM, St5 + St6 + St7 | 39.3 | 13.1 | 21.3 | 7.8 |

TABLE 3

Effect of different levels of Ethanol on FPM in FP/HFA134a solution aerosols
(valve size effect ignored)
All tested with 0.22 mm actuator, except HFA134a suspension product tested with 0.50 mm actuator
% Results Cascade Impaction

| Formulation | Ethanol only | | | | Ethanol and 1% glycerol | | | | HFA134a* |
|---|---|---|---|---|---|---|---|---|---|
| Ethanol conc. | 10% w/w | 16% w/w | 21% w/w | 35% w/w | 10% w/w | 16% w/w | 21% w/w | 35% w/w | — |
| Valve size | 100 μl | 63 μl | 50 μl | 63 μl | 100 μl | 63 μl | 50 μl | 63 μl | 50 μl |
| Product | FP | FP | FP | FP | FP | FP | FP | FP | FP |
| Product strength | 50 μg | 50 μg | 50 μg | 125 μg | 50 μg | 50 μg | 50 μg | 125 μg | 50 μg |
| Device | 10.7 | 10.1 | 10.9 | 12.1 | 9.9 | 8.6 | 10.4 | 12.6 | 13.3 |
| Throat | 23.9 | 35.8 | 43.6 | 62.6 | 30.4 | 38.8 | 46.4 | 63.1 | 27.2 |
| Stage 0 | 8.5 | 5.2 | 5.8 | 6.5 | 6.5 | 6.3 | 5.8 | 5.8 | 3.2 |
| Stage 1 | 0.6 | 0.7 | 0.6 | 0.0 | 1.3 | 1.0 | 1.2 | 1.0 | 1.6 |

TABLE 3-continued

Effect of different levels of Ethanol on FPM in FP/HFA134a solution aerosols
(valve size effect ignored)
All tested with 0.22 mm actuator, except HFA134a suspension product tested with 0.50 mm actuator
% Results Cascade Impaction

| | | | | | | | | | |
|---|---|---|---|---|---|---|---|---|---|
| Stage 2 | 0.4 | 0.5 | 0.4 | 0.0 | 2.1 | 1.7 | 1.6 | 1.0 | 2.2 |
| Stage 3 | 0.6 | 0.5 | 0.6 | 0.9 | 10.3 | 8.2 | 7.6 | 2.9 | 6.4 |
| Stage 4 | 1.7 | 1.4 | 2.1 | 1.9 | 14.4 | 12.6 | 10.4 | 4.9 | 19.7 |
| Stage 5 | 18.4 | 15.3 | 14.4 | 6.5 | 16.2 | 15.9 | 10.6 | 4.9 | 22.5 |
| Stage 6 | 16.2 | 16.0 | 11.5 | 4.7 | 4.6 | 3.3 | 3.2 | 1.9 | 2.8 |
| Stage 7 | 10.3 | 8.0 | 5.8 | 1.9 | 2.7 | 2.1 | 1.6 | 1.0 | 0.6 |
| Filter | 8.8 | 6.4 | 4.3 | 2.8 | 1.7 | 1.4 | 1 | 1.0 | 0.4 |
| Total | 100.0 | 100.0 | 100.0 | 100.0 | 100.0 | 100.0 | 100.0 | 100.0 | 100 |
| Total ex-device | 89.3 | 89.8 | 89.1 | 87.8 | 90.1 | 91.3 | 89.6 | 87.4 | 86.7 |
| FPM, St3 + St4 + St5 | 20.7 | 17.2 | 17.1 | 9.3 | 40.9 | 36.7 | 28.6 | 12.7 | 48.7 |
| FPM, St5 + St6 + St7 | 44.9 | 39.3 | 31.7 | 13.1 | 23.5 | 21.3 | 15.4 | 7.8 | 25.9 |

*Flixotide Evohaler Suspension Formulation

TABLE 4

Cascade Impaction analysis of FP/HFA134a 125 µg solution aerosols containing 35%
ethanol or 35% ethanol and 1% glycerol (0.22 mm actuator 63 µl m/c Valois valve)

| Formulation | Ethanol only | | | Ethanol and glycerol | | |
|---|---|---|---|---|---|---|
| Stage of Use | BoU (act. 1–10) | | | BoU (act. 1–10) | | |
| Sample ID | FP125/A3/1 | FP125/A3/1 | Mean | FP125/A3/1 | FP125/A3/2 | Mean |
| Device | 13.6 | 10.7 | 12.2 | 14.4 | 10.9 | 12.7 |
| Throat | 59.2 | 73.9 | 66.6 | 64.7 | 64.4 | 64.6 |
| Stage 0 | 6.8 | 6.9 | 6.9 | 5.6 | 5.9 | 5.8 |
| Stage 1 | 0.5 | 0.3 | 0.4 | 0.5 | 0.5 | 0.5 |
| Stage 2 | 0.3 | 0.1 | 0.2 | 0.6 | 0.8 | 0.7 |
| Stage 3 | 0.5 | 0.4 | 0.5 | 2.4 | 2.6 | 2.5 |
| Stage 4 | 2.2 | 1.7 | 2.0 | 4.8 | 5.0 | 4.9 |
| Stage 5 | 8.5 | 6.1 | 7.3 | 5.5 | 5.0 | 5.3 |
| Stage 6 | 5.2 | 4.1 | 4.7 | 2.0 | 1.7 | 1.9 |
| Stage 7 | 2.4 | 1.8 | 2.1 | 1.1 | 0.8 | 1.0 |
| Filter | 2.1 | 2.7 | 2.4 | 0.7 | 0.5 | 0.6 |
| Total | 101.3 | 108.7 | 105.0 | 102.3 | 98.1 | 100.2 |
| Total ex-device | 87.7 | 98.0 | 92.9 | 87.9 | 87.2 | 87.6 |
| FPM, St3 + St4 + St5 | 11.2 | 8.2 | 9.7 | 12.7 | 12.6 | 12.7 |
| FPM, St5 + St6 + St7 | 16.1 | 12.0 | 14.1 | 8.6 | 7.5 | 8.1 |

All means, Totals and FPMs were calculated by Excel on rounded individual data
A3 = Actuator 0.22 mm × 0.65 mm

TABLE 5

Cascade Impaction analysis of FP/HFA134a 50 µg solution aerosols containing 16% ethanol
or 16% ethanol and 1% glycerol (63 µl m/c Valois valve DF60 MK37)

| Formulation | Ethanol only | | | | | | | | | Ethanol and glycerol | | | | | | FP/134a 50 µg Initial, BoU |
|---|---|---|---|---|---|---|---|---|---|---|---|---|---|---|---|---|
| Stage of Use | BoU (act.1–10) | | | | | | | | | BoU (act.1–10) | | | | | | |
| Product Actuator | FP50 0.50 mm | FP50 0.50 mm | Mean | FP50 0.33 mm | FP50 0.33 mm | Mean | FP50 0.22 mm | FP50 0.22 mm | Mean | FP50 0.33 mm | FP50 0.33 mm | Mean | FP50 0.22 mm | FP50 0.22 mm | Mean | Mean 0.50 mm |
| Device | 4.2 | 4.2 | 4.2 | 5.3 | 4.2 | 4.8 | 5.2 | 3.3 | 4.3 | 4.7 | 4.4 | 4.6 | 4.4 | 3.7 | 4.1 | 6.6 |
| Throat | 32.4 | 32.3 | 32.4 | 25.1 | 25.9 | 25.5 | 13.9 | 16.4 | 15.2 | 26.2 | 28.5 | 27.4 | 16.3 | 17.8 | 17.1 | 13.5 |
| Stage 0 | 1.4 | 1.4 | 1.4 | 1.0 | 1.7 | 1.4 | 2.3 | 2.1 | 2.2 | 1.0 | 1.3 | 1.2 | 3.6 | 2.6 | 3.1 | 1.6 |
| Stage 1 | 0.1 | 0.1 | 0.1 | 0.1 | 0.1 | 0.1 | 0.3 | 0.3 | 0.3 | 0.2 | 0.4 | 0.3 | 0.6 | 0.4 | 0.5 | 0.8 |
| Stage 2 | 0.0 | 0.1 | 0.1 | 0.1 | 0.1 | 0.1 | 0.2 | 0.2 | 0.2 | 0.3 | 0.4 | 0.4 | 1.0 | 0.7 | 0.9 | 1.1 |
| Stage 3 | 0.1 | 0.1 | 0.1 | 0.1 | 0.3 | 0.2 | 0.2 | 0.2 | 0.2 | 1.4 | 1.5 | 1.5 | 4.3 | 3.5 | 3.9 | 3.2 |
| Stage 4 | 0.3 | 0.3 | 0.3 | 0.3 | 0.5 | 0.4 | 0.7 | 0.5 | 0.6 | 2.6 | 2.5 | 2.6 | 6.2 | 5.5 | 5.9 | 9.8 |
| Stage 5 | 1.8 | 2.0 | 1.9 | 3.6 | 3.9 | 3.8 | 6.4 | 6.5 | 6.5 | 4.0 | 3.5 | 3.8 | 7.5 | 7.0 | 7.3 | 11.2 |
| Stage 6 | 1.5 | 1.6 | 1.6 | 3.5 | 3.5 | 3.5 | 6.8 | 6.8 | 6.8 | 1.0 | 0.9 | 1.0 | 1.8 | 1.4 | 1.6 | 1.4 |
| Stage 7 | 0.9 | 1.0 | 1.0 | 2.1 | 2.0 | 2.1 | 3.4 | 3.4 | 3.4 | 0.6 | 0.5 | 0.6 | 1.0 | 0.9 | 1.0 | 0.3 |
| Filter | 1.3 | 1.4 | 1.4 | 2.1 | 2.6 | 2.4 | 2.7 | 2.7 | 2.7 | 0.5 | 0.4 | 0.5 | 0.7 | 0.6 | 0.7 | 0.2 |
| Total | 44.0 | 44.5 | 44.3 | 43.3 | 44.8 | 44.1 | 42.1 | 42.4 | 42.3 | 42.5 | 44.3 | 43.4 | 47.4 | 44.1 | 45.8 | 44.9 |
| Total ex-device | 39.0 | 39.0 | 39.0 | 37.0 | 40.0 | 38.5 | 36.0 | 38.0 | 37.0 | 38.0 | 39.0 | 38.5 | 44.0 | 43.0 | 43.5 | 43.3 |

TABLE 5-continued

Cascade Impaction analysis of FP/HFA134a 50 μg solution aerosols containing 16% ethanol
or 16% ethanol and 1% glycerol (63 μl m/c Valois valve DF60 MK37)

| | | | | | | | | | | | | | | | | |
|---|---|---|---|---|---|---|---|---|---|---|---|---|---|---|---|---|
| FPM, St3 + St4 + St5 | 2.0 | 2.0 | 2.0 | 4.0 | 4.0 | 4.0 | 7.0 | 7.0 | 7.0 | 8.0 | 8.0 | 8.0 | 18.0 | 17.0 | 17.5 | 17.3 |
| FPM, St5 + St6 + St7 | 4.2 | 4.6 | 4.4 | 9.2 | 9.4 | 9.3 | 16.6 | 16.7 | 16.7 | 5.6 | 4.9 | 5.3 | 10.3 | 9.3 | 9.8 | 9.6 |

All means, Totals and FPMs were calculated by Excel on rounded individual data
*Flixotide Evohaler suspension formulation

TABLE 6

Cascade Impaction analysis of FP/HFA134a 50 μg solution aerosols containing various solubilising agents
(100 μl Valois valve, Bespak 0.22 mm × 0.65 mm actuator)

| Formulation Stage of Use | FP 50 μg BoU (act. 1–10) | | FP 50 μg BoU (act. 1–10) | | FP 50 μg BoU (act. 1–10) | |
|---|---|---|---|---|---|---|
| Valve | 100 μl | 100 μl | 100 μl | 100 μl | 100 μl | 100 μl |
| LVC | — | 1% glycerol | — | 1% glycerol | — | 1% glycerol |
| Solvent | 15% methylal* | 15% methylal | 15% ethyl acetate | 15% ethyl acetate | 10% ethanol | 10% ethanol |
| Device | 5.9 | 6.2 | 9.0 | 6.4 | 4.3 | 4.4 |
| Throat | 5.8 | 6.3 | 5.3 | 13.8 | 15.2 | 14.0 |
| Stage 0 | 1.4 | 3.9 | 1.2 | 1.6 | 2.2 | 3.3 |
| Stage 1 | 0.5 | 0.8 | 0.5 | 0.6 | 0.3 | 0.7 |
| Stage 2 | 0.6 | 0.7 | 0.5 | 0.8 | 0.2 | 1.0 |
| Stage 3 | 0.9 | 1.4 | 1.1 | 1.7 | 0.2 | 5.3 |
| Stage 4 | 1.6 | 2.3 | 0.8 | 1.8 | 0.6 | 8.1 |
| Stage 5 | 6.9 | 10.3 | 1.9 | 9.2 | 6.5 | 8.8 |
| Stage 6 | 8.8 | 7.6 | 5.0 | 6.2 | 6.8 | 2.4 |
| Stage 7 | 6.0 | 3.8 | 4.4 | 3.2 | 3.4 | 1.3 |
| Filter | 4.8 | 2.0 | 3.0 | 2.0 | 2.7 | 0.7 |
| Total | 43.2 | 45.1 | 32.4 | 47.1 | 42.3 | 49.8 |
| Total ex-device | 37.3 | 39.0 | 23.4 | 40.7 | 37.0 | 45.5 |
| FPM, St3 + St4 + St5 | 9.4 | 13.9 | 3.7 | 12.7 | 7.0 | 22.2 |

*Result based on one can only (can 2 data rejected as an atypical result)
LVC = low volatility component

TABLE 7

Cascade Impaction analysis of FP/HFA134a 50 μg solution aerosols containing various low volatility components
(63 μl m/c Valols valve DF60 or 100 μl Valols valve, Bespak 0.22 mm × 0.65 mm actuator)

| Formulation Stage | FP50 μg HFA134a BoU (act. 1–10) | | FP50 μg HFA134a BoU (act. 1–10) | | FP50 μg HFA134a BoU (act. 1–10) | | FP50 μg HFA134a BoU (act. 1–10) | |
|---|---|---|---|---|---|---|---|---|
| of Use Valve | 63 μl | Normalised for 100 μl | 63 μl | Normalised for 100 μl | 63 μl | Normalised for 100 μl | 63 μl | Normalised for 100 μl |
| LVC | 1% propylene glycol | 1% propylene glycol | 1% PEG200 | 1% PEG200 | 1% PEG400 | 1% PEG400 | 1% glycerol | 1% glycerol |
| Solvent | 10% ethanol | 10% ethanol | 10% ethanol | 10% ethanol | 10% ethanol | 10% ethanol | 10% ethanol | 10% ethanol |
| Device | 2.2 | 3.5 | 2.3 | 3.7 | 2.0 | 3.1 | 1.7 | 2.7 |
| Throat | 7.3 | 11.6 | 6.1 | 9.7 | 5.5 | 8.7 | 5.5 | 8.7 |
| Stage 0 | 0.7 | 1.1 | 0.8 | 1.3 | 0.9 | 1.4 | 1.2 | 1.9 |
| Stage 1 | 0.3 | 0.5 | 0.3 | 0.5 | 0.2 | 0.4 | 0.3 | 0.5 |
| Stage 2 | 0.6 | 1.0 | 0.6 | 1.0 | 0.6 | 1.0 | 0.7 | 1.1 |
| Stage 3 | 3.1 | 4.9 | 3.5 | 5.6 | 2.9 | 4.6 | 3.0 | 4.8 |
| Stage 4 | 3.6 | 5.7 | 4.7 | 7.5 | 5.2 | 8.3 | 5.5 | 8.7 |
| Stage 5 | 3.7 | 5.9 | 5.7 | 9.0 | 6.4 | 10.2 | 5.2 | 8.3 |
| Stage6 | 1.0 | 1.6 | 1.7 | 2.7 | 1.7 | 2.7 | 1.5 | 2.4 |
| Stage 7 | 1.4 | 2.2 | 0.9 | 1.4 | 1.0 | 1.5 | 0.7 | 1.1 |
| Filter | 0.6 | 1.0 | 0.1 | 0.2 | 0.6 | 0.9 | 0.4 | 0.6 |
| Total | 24.3 | 38.6 | 26.5 | 42.1 | 27.0 | 42.8 | 25.4 | 40.3 |
| Total ex-device | 22.1 | 35.1 | 24.2 | 38.4 | 25.0 | 39.7 | 23.8 | 37.8 |
| FPM, St3 + St4 + St15 | 10.3 | 16.3 | 13.8 | 21.9 | 14.5 | 23.0 | 13.6 | 21.6 |

LVC = low volatility component

TABLE 8

Cascade Impaction analysis of FP 50 µg solution aerosols containing various propellants
(63 µl m/c Valois valve DF60 or 100 µl Valois valve, Bespak 0.22 mm × 0.65 mm actuator)

| Formulation<br>Stage of Use | FP50 µg HFA227ea<br>BoU (act. 1–10) | | FP50 µg HFA227ea<br>BoU (act. 1–10) | | FP50µ HFA134a<br>BoU (act. 1–10) | |
|---|---|---|---|---|---|---|
| Valve | 63 µl | Normalised<br>for 100 µl | 63 µl | Normalised<br>for 100 µl | 63 µl | Normalised<br>for 100 µl |
| LVC | — | — | 1% glycerol | 1% glycerol | 1% glycerol | 1% glycerol |
| Solvent | 18% ethanol | 18% ethanol | 18% ethanol | 18% ethanol | 10% ethanol | 10% ethanol |
| Device | 2.4 | 3.8 | 2.4 | 3.8 | 1.7 | 2.7 |
| Throat | 14.4 | 22.9 | 13.8 | 21.8 | 5.5 | 8.7 |
| Stage 0 | 2.0 | 3.2 | 2.3 | 3.7 | 1.2 | 1.9 |
| Stage 1 | 0.3 | 0.5 | 0.4 | 0.6 | 0.3 | 0.5 |
| Stage 2 | 0.2 | 0.3 | 0.7 | 1.1 | 0.7 | 1.1 |
| Stage 3 | 0.2 | 0.3 | 2.4 | 3.7 | 3.0 | 4.8 |
| Stage 4 | 0.4 | 0.6 | 2.9 | 4.6 | 5.5 | 8.7 |
| Stage 5 | 3.0 | 4.8 | 2.4 | 3.8 | 5.2 | 8.3 |
| Stage 6 | 2.7 | 4.3 | 0.6 | 1.0 | 1.5 | 2.4 |
| Stage 7 | 1.4 | 2.2 | 0.3 | 0.5 | 0.7 | 1.1 |
| Filter | 1.2 | 1.9 | 0.1 | 0.2 | 0.4 | 0.6 |
| Total | 28.1 | 44.6 | 28.2 | 44.8 | 25.4 | 40.3 |
| Total ex-device | 25.7 | 40.8 | 25.8 | 41.0 | 23.8 | 37.8 |
| FPM, St3 + St4 + St5 | 3.6 | 5.7 | 7.7 | 12.1 | 13.6 | 21.6 |

LVC = low volatility component

TABLE 9

Cascade Impaction analysis of FP 25 µg solution aerosols containing various propellants
(63 µl m/c Valois valve DF60 or 100 µl Valois valve, Bespak 0.22 mm × 0.65 mm actuator)

| Formulation<br>Stage of Use | FP25 µg HFA134a<br>BoU (act. 1–10) | | FP25 µg HFA134a<br>BoU (act. 1–10) | | FP25µ HFA227ea<br>BoU (act. 1–10) | | FP25µ HFA227ea<br>BoU (act. 1–10) | |
|---|---|---|---|---|---|---|---|---|
| Valve | 63 µl | Normalised<br>for 100 µl | 63 µl | Normalised<br>for 100 µl | 63 µl | Normalised<br>for 100 µl | 63 µl | Normalised<br>for 100 µl |
| LVC | — | — | 1% glycerol | 1% glycerol | — | — | 1% glycerol | 1% glycerol |
| Solvent | 7% ethanol | 7% ethanol | 7% ethanol | 7% ethanol | 14% ethanol | 14% ethanol | 14% ethanol | 14% ethanol |
| Device | 1.3 | 2.1 | 1.1 | 1.7 | 1.1 | 1.7 | 1.0 | 1.6 |
| Throat | 1.3 | 2.1 | 1.6 | 2.5 | 4.2 | 6.7 | 4.5 | 7.1 |
| Stage 0 | 0.1 | 0.2 | 0.3 | 0.5 | 1.1 | 1.7 | 1.5 | 2.4 |
| Stage 1 | 0.0 | 0.0 | 0.1 | 0.2 | 0.1 | 0.2 | 0.3 | 0.5 |
| Stage 2 | 0.0 | 0.0 | 0.2 | 0.3 | 0.1 | 0.2 | 0.4 | 0.6 |
| Stage 3 | 0.0 | 0.0 | 1.1 | 1.7 | 0.1 | 0.2 | 1.6 | 2.5 |
| Stage 4 | 0.1 | 0.2 | 2.7 | 4.3 | 0.1 | 0.2 | 1.9 | 3.0 |
| Stage 5 | 1.0 | 1.6 | 4.1 | 6.5 | 1.9 | 3.0 | 1.5 | 2.4 |
| Stage 6 | 2.8 | 4.4 | 1.3 | 2.1 | 2.4 | 3.8 | 0.4 | 0.6 |
| Stage 7 | 2.4 | 3.8 | 0.6 | 1.0 | 1.4 | 2.2 | 0.2 | 0.3 |
| Filter | 1.9 | 3.0 | 0.3 | 0.5 | 1.0 | 1.6 | 0.2 | 0.3 |
| Total | 10.8 | 17.1 | 13.3 | 21.1 | 13.3 | 21.1 | 13.3 | 21.1 |
| Total ex-device | 9.5 | 15.1 | 12.2 | 19.4 | 12.3 | 19.5 | 12.3 | 19.5 |
| FPM, St3 + St4 + St5 | 1.1 | 1.7 | 7.8 | 12.4 | 2.1 | 3.3 | 4.9 | 7.8 |

LVC = low volatility component

What is claimed is:

1. A metered dose inhaler which comprises a canister fitted with a metering valve which contains a pharmaceutical solution aerosol formulation which comprises:
   (i) fluticasone propionate and
   (ii) a hydrofluoroalkane (HFA) propellant,
   characterised in that the fluticasone propionate is completely dissolved in the formulation; wherein the canister is fitted into a channelling device which comprises a mouthpiece actuator having an actuator exit orifice of diameter 0.25 mm or less.

2. A metered dose inhaler according to claim 1 wherein the formulation comprises:
   (i) fluticasone propionate;
   (ii) a hydrofluoroalkane (HFA) propellant;
   (iii) a low volatility component present in the formulation at a concentration of 0.5 to 3% w/w, to increase the mass median aerodynamic diameter (MMAD) of the aerosol particles on actuation of an inhaler; and
   (iv) a solubilisation agent in sufficient quantity to solubilise the fluticasone propionate in the formulation.

3. A metered dose inhaler according to claim 1 wherein the hydrofluoroalkane (HFA) propellant is 1,1,1,2-tetrafluoroethane (HFA134a).

4. A metered dose inhaler according to claim 1 wherein the formulation contains a low volatility component which is glycerol, propylene glycol or polyethylene glycol.

5. A metered dose inhaler according to claim 4 wherein the formulation contains a low volatility component which is polyethylene glycol.

6. A metered dose inhaler according to claim 4 wherein the formulation contains a low volatility component which is glycerol.

7. A metered dose inhaler according to claim 1 wherein the formulation comprises:
(i) fluticasone propionate;
(ii) 1,1,1,2-tetrafuoroethane (HFA134a);
(iii) 0.5–3% (w/w) glycerol; and
(iv) a solubilisation agent in sufficient quantity to solubilise the fluticasone propionate in the formulation.

8. A metered dose inhaler according to claim 1 wherein the formulation contains between 0.8 and 1.6% (w/w) glycerol.

9. A metered dose inhaler according to claim 8 wherein the formulation contains between 1.0 and 1.6% (w/w) glycerol.

10. A metered dose inhaler according to claim 9 wherein the formulation contains between 1.0 and 1.6% (w/w) glycerol.

11. A metered dose inhaler according to claim 9 wherein the formulation contains 1.0% (w/w) glycerol.

12. A metered dose inhaler according to claim 1 wherein the concentration of fluticasone propionate in the formulation is 0.025 to 0.15% w/v.

13. A metered dose inhaler according to claim 12 wherein the concentration of fluticasone propionate in the formulation is 0.035 to 0.15% w/v.

14. A metered dose inhaler according to claim 13 wherein the concentration of fluticasone propionate in the formulation is 0.04 to 0.1% w/v.

15. A metered dose inhaler according to claim 12 wherein the concentration of fluticasone propionate in the formulation is 0.025 to 0.04% w/v.

16. A metered dose inhaler according to claim 1 wherein a solubilisation agent is present in the formulation which is ethanol or propylene glycol.

17. A metered dose inhaler according to claim 1 wherein a solubilisation agent is present in the formulation which is an alkane or ether.

18. A metered dose inhaler according to claim 1 wherein a solubilisation agent is present in the formulation which is dimethoxymethane.

19. A metered dose inhaler according to claim 1 wherein a solubilisation agent is present in the formulation which is ethylacetate.

20. A metered dose inhaler according to claim 16 wherein a solubilisation agent is present in the formulation which is ethanol.

21. A metered dose inhaler according to claim 20 wherein the concentration of ethanol in the formulation is 5 to 30% w/w.

22. A metered dose inhaler according to claim 21 wherein the concentration of ethanol in the formulation is 10 to 20% w/w.

23. A metered dose inhaler according to claim 21 wherein the concentration of ethanol in the formulation is 7 to 16% w/w.

24. A metered dose inhaler according to claim 21 wherein the concentration of ethanol in the formulation is 7 to 11% w/w.

25. A metered dose inhaler according to claim 21 wherein the concentration of ethanol in the formulation is 7 to 8% w/w.

26. A metered dose inhaler according to claim 18 wherein the concentration of solubilisation agent in the formulation is 14 to 16% w/w.

27. A metered dose inhaler according to claim 1 comprising as canister an aluminium can which is anodised, lacquer-coated and/or plastic coated.

28. A metered dose inhaler according to claim 27 wherein the canister is coated with a fluorocarbon polymer.

29. A metered dose inhaler according to claim 1 wherein the canister is fitted with a metering valve of metering volume 100 µl.

30. A metered dose inhaler according to claim 1 wherein the channelling device comprises a mouthpiece actuator having an actuator orifice of diameter 0.15–0.22 mm.

31. A method of treating respiratory disorders which comprises administration by inhalation of an effective amount of a pharmaceutical aerosol formulation by means of a metered dose inhaler according to claim 1.

32. A metered dose inhaler according to claim 19 wherein the concentration of solubilising agent in the formulation is 14 to 16% w/w.

33. A metered dose inhaler according to claim 13 wherein the propellant is 1,1,1,2-tetrafluoroethane and a solubilising agent is present in the formulation which is ethanol.

34. A metered dose inhaler according to claim 14 where in the propellant is 1,1,1,2-tetrafluoroethane and a solubilising agent is present in the formulation which is ethanol.

35. A metered dose inhaler according to claim 33 wherein a low volatility component to increase the mass median aerodynamic diameter (MMAD) of the aerosol particles on actuation of the inhaler is present in the formulation which is glycerol at a concentration of 0.5–3% w/w.

* * * * *